(12) United States Patent
Brattoli et al.

(10) Patent No.: US 12,266,196 B2
(45) Date of Patent: Apr. 1, 2025

(54) METHOD AND SYSTEM FOR ANALYZING PATHOLOGY IMAGE

(71) Applicant: Lunit Inc., Seoul (KR)

(72) Inventors: Biagio Brattoli, Seoul (KR); Chan-Young Ock, Seoul (KR); Wonkyung Jung, Seoul (KR); Soo Ick Cho, Seoul (KR); Kyunghyun Paeng, Seoul (KR); Dong Geun Yoo, Seoul (KR)

(73) Assignee: Lunit Inc., Seoul (KR)

( * ) Notice: Subject to any disclaimer, the term of this patent is extended or adjusted under 35 U.S.C. 154(b) by 0 days.

(21) Appl. No.: 18/491,314

(22) Filed: Oct. 20, 2023

(65) Prior Publication Data
US 2024/0046670 A1 Feb. 8, 2024

Related U.S. Application Data

(63) Continuation of application No. PCT/KR2022/010321, filed on Jul. 14, 2022.

(30) Foreign Application Priority Data

Jul. 14, 2021 (KR) .................. 10-2021-0092181
Jul. 14, 2022 (KR) .................. 10-2022-0087202

(51) Int. Cl.
*G06V 20/69* (2022.01)
*G06V 10/22* (2022.01)
*G06V 10/98* (2022.01)

(52) U.S. Cl.
CPC .......... *G06V 20/695* (2022.01); *G06V 10/235* (2022.01); *G06V 10/993* (2022.01)

(58) Field of Classification Search
CPC ... G06V 20/695; G06V 10/235; G06V 10/993
See application file for complete search history.

(56) References Cited

U.S. PATENT DOCUMENTS

2010/0254589 A1* 10/2010 Gallagher ............ G06V 20/695
                                                     382/133
2019/0080450 A1* 3/2019 Arar .................... G06V 20/695
(Continued)

FOREIGN PATENT DOCUMENTS

CN      115668284 A  *  1/2023   ......... G06K 9/00147
EP      3588382 A1   *  1/2020   ........... A61B 5/7267
(Continued)

OTHER PUBLICATIONS

Computational pathology for musculoskeletal conditions using machine learning: advances, trends, and challenges—2022 (Year: 2022).*
(Continued)

*Primary Examiner* — Nizar N Sivji
(74) *Attorney, Agent, or Firm* — Sughrue Mion, PLLC

(57) ABSTRACT

Provided is a method for analysing a pathology image, which is performed by at least one processor and includes acquiring a pathology image, inputting the acquired pathology image into a machine learning model and acquiring an analysis result for the pathology image from the machine learning model, and outputting the acquired analysis result, in which the machine learning model is a model trained by using a training data set generated based on a first pathology data set associated with a first domain and a second pathology data set associated with a second domain different from the first domain.

18 Claims, 21 Drawing Sheets

(56) References Cited

U.S. PATENT DOCUMENTS

| | | | |
|---|---|---|---|
| 2020/0321118 A1 | 10/2020 | Kim et al. | |
| 2020/0388028 A1* | 12/2020 | Agus | G16H 50/20 |
| 2021/0073986 A1* | 3/2021 | Kapur | G06T 7/11 |
| 2021/0350176 A1* | 11/2021 | Klaiman | G06T 7/0012 |
| 2023/0206698 A1* | 6/2023 | Huang | G06V 10/454 |
| | | | 382/118 |

FOREIGN PATENT DOCUMENTS

| | | | |
|---|---|---|---|
| KR | 10-1889725 B1 | 8/2018 | |
| KR | 10-2039138 B1 | 10/2019 | |
| KR | 10-2246319 B1 | 5/2021 | |
| WO | 2020182710 A1 | 9/2020 | |
| WO | WO-2022015819 A1 * | 1/2022 | G06F 18/2155 |
| WO | WO-2022038527 A1 * | 2/2022 | G06N 3/045 |
| WO | WO-2022251556 A1 * | 12/2022 | |
| WO | WO-2023043709 A1 * | 3/2023 | |
| WO | WO-2023081260 A1 * | 5/2023 | |

OTHER PUBLICATIONS

Heather D. Couture, et al., "Image analysis with deep learning to predict breast cancer grade, ER status, histologic subtype, and intrinsic subtype", npj Nature Partner Journal Breast Cancer, 2018, vol. 4, Article No. 30, pp. 1-8.

International Search Report for PCT/KR2022/010321 dated Oct. 25, 2022.

Written Opinion for PCT/KR2022/010321 dated Oct. 25, 2022.

* cited by examiner

310

410

METHOD AND SYSTEM FOR ANALYZING PATHOLOGY IMAGE

TECHNICAL FIELD

The present disclosure relates to a method and system for analysing a pathology image, and specifically, to a method and system for analysing various types of pathology images using a machine learning model.

BACKGROUND

In the field of pathology, method is used in which tissues are stained based on various staining methods to generate pathology slides, and pathologist visually evaluates the pathology slides in order to acquire and analyse biological information from the pathological tissues.

Among these methods, immunohistochemistry (IHC) is a method for binding an enzyme or fluorescent dye as a secondary antibody to an antibody that reacts to a target antigen and staining the specific tissue with this bound antibody. When a specific tissue is stained according to immunohistochemistry, the antibody binds to cells expressing the target antigen corresponding to the target, and this binding reaction activates the secondary antibody, causing a staining reaction. The pathologist may identify the stained cells under a microscope and evaluate the cells. For example, the pathologist may evaluate and quantify an amount of staining expressed, etc. to derive meaningful information from the tissue.

However, the method that the pathologist reads stained pathology slides and evaluates and quantifies the results not only involves human subjective factors, but also requires a lot of labor and time, and accordingly, researches have been conducted recently to read pathology slides using artificial intelligence algorithms such as deep learning. For this purpose, pathology slides are scanned and stored as digital pathology images, and artificial intelligence algorithms are trained using these pathology images.

However, artificial intelligence algorithms require a large amount of training data to predict accurate results. However, since pathology images input to the artificial intelligence algorithm must be labeled with medical knowledge, this labeling task must be performed by medical experts, which incurs cost and time to build training data.

Meanwhile, in the medical field, biomarkers associated with many new drugs are being developed. There is a large amount of accumulated clinical data associated with biomarkers already used in clinical practice (e.g., clinical data associated with PD-L1 IHC, HER2 IHC, etc.), so it is relatively easy to generate the training data necessary for training artificial intelligence algorithms. However, because there is little clinical data associated with new biomarkers, it may not be possible to ensure a sufficient amount of training data in a short period of time to analyse slide images stained with new types of IHC staining methods.

In addition, in the case of certain cancer types, the prevalence rate is low, so the absolute number of samples may be smaller compared to other cancer types that occur relatively commonly. In this case, because the artificial intelligence model has to be trained using relatively small amount of data, the artificial intelligence model may not be properly trained or may be trained to be biased toward a specific training data set.

SUMMARY

The present disclosure provides a method, computer program stored in a recording medium, and apparatus (system) for analysing pathology slides, which are capable of accurately analysing various types of pathology images.

The present disclosure may be implemented in various ways, including a method, an apparatus (system), or a computer program stored in a computer-readable storage medium, and a computer-readable storage medium in which the computer program is stored.

A method for analysing a pathology image is provided, which may be performed by at least one processor and include acquiring a pathology image, inputting the acquired pathology image into a machine learning model and acquiring an analysis result for the pathology image from the machine learning model, and outputting the acquired analysis result, in which the machine learning model may be a model trained by using a training data set generated based on a first pathology data set associated with a first domain and a second pathology data set associated with a second domain different from the first domain.

In addition, the method for analysing the pathology image may further include, prior to acquiring the pathology image, acquiring a first pathology data set including a first type of pathology image and a second pathology data set including a second type of pathology image, generating a training data set based on the first pathology data set and the second pathology data set, and training a machine learning model using the generated training data set.

In addition, the generating the training data set may include associating items associated with the first type of pathology image with items associated with the second type of pathology image based on at least one of a staining expression grade or a region of interest, and generating a training data set including the associated items.

In addition, the associating the items may include extracting a first item associated with a tumor tissue region included in the first type of pathology image and a second item associated with a non-tumor tissue region included in the first type of pathology image, extracting a third item associated with a tumor tissue region included in the second type of pathology image and a fourth item associated with a non-tumor tissue region included in the second type of pathology image, and associating the extracted first item with the extracted third item, and associating the extracted second item with the extracted fourth item.

In addition, the associating the items may include extracting a fifth item associated with a first expression range and a sixth item associated with a second expression range from items representing intensities of each staining expression of pixels included in the first type of pathology image, identifying a seventh item associated with the first expression range and an eighth item associated with the second expression range from the items representing intensities of each staining expression of pixels included in the second pathology data set, and associating the fifth item and the seventh item and associating the sixth item and the eighth item.

In addition, the associating the items may include associating at least one object class representing a type of cell included in the first type of pathology image with at least one object class representing a type of cell included in the second type of pathology image, or associating at least one object class representing intensity of staining expression of cell included in the first type of pathology image with at least one object class representing intensity of staining expression of cell included in the second type of pathology image.

In addition, the generating the training data set based on the first pathology data set and the second pathology data set may include extracting patches from the first pathology data set and the second pathology data set, and generating a training data set including the patches, and the training the machine learning model using the generated training data set may include fetching, from the labeled patches extracted from the first pathology data set, the corresponding number of first type of image patches corresponding to the number of first sampling, fetching, from the labeled patches extracted from the second pathology data set, the corresponding number of a second type of image patches corresponding to the number of second sampling, generating a batch based on the first type of image patches and the second type of image patches, and training the machine learning model using the batch.

In addition, the generating the training data set based on the first pathology data set and the second pathology data set may include extracting a first type of image patches from the first pathology data set, extracting a second type of image patches from the second pathology data set, and copying a predetermined number of the first type of image patches and including the image patches in the training data set.

In addition, the training the machine learning model may include adjusting a size of at least one of the first type of pathology image or the second type of pathology image, and training the machine learning model using training data including at least one pathology image that is adjusted in size.

In addition, the training the machine learning model may include removing pixels corresponding to a predetermined range from pixels included in at least one of the first type of pathology image and the second type of pathology image.

In addition, the training the machine learning model may include inverting at least one of the first type of pathology image or the second type of pathology image left and right or up and down, and training the machine learning model using training data including the inverted pathology image.

In addition, the training the machine learning model may include removing or modifying pixels in a predetermined range from among pixels included in at least one of the first type of pathology image and the second type of pathology image, and training the machine learning model using training data including a pathology image in which the pixels in the predetermined range are removed or modified.

In addition, the training the machine learning model may include converting a color of pixels included in at least one of the first type of pathology image or the second type of pathology image, and training the machine learning model using training data including at least one pathology image in which the color of the pixels are converted.

In addition, the training the machine learning model may include determining target training data from the training data set, inputting the target training data into the machine learning model, and acquiring an output value from the machine learning model, acquiring a reference value for the target training data using annotation information included in at least one of the first pathology data set and the second pathology data set, and feeding back a loss value between the output value and the acquired reference value to the machine learning model.

In addition, the machine learning model may include a plurality of analysis models that output different types of analysis results, and the acquiring the analysis result may include identifying, from the acquired pathology image, staining color and location where the staining is expressed, determining one of the plurality of analysis models as the target analysis model based on the identified staining color and expression location, and inputting the pathology image into the determined target analysis model and acquiring, from the target analysis model, an analysis result of staining intensity at the expressed location.

In addition, the machine learning model may include a plurality of analysis models that output different types of analysis results, and the acquiring the analysis result may include determining one of the plurality of analysis models as the target analysis model based on user input information, and inputting the pathology image into a target analysis model and acquiring an analysis result for the pathology image from the target analysis model.

In addition, the machine learning model may output an analysis result that includes at least one of a type of cell or an evaluation index of the cell, and the cell evaluation index may include at least one of positive or negative result for the cell, a staining expression grade for the cell, a value indicating a degree of staining expression for the cell, or statistical information on staining expression of the cell.

A computer-readable non-transitory recording medium recording instructions for executing the method described above on a computer may be provided.

An information processing system is provided, which may include a memory, and at least one processor connected to the memory and configured to execute at least one computer-readable program included in the memory, in which the at least one program may include instructions for acquiring a pathology image; inputting the acquired pathology image into a machine learning model and acquiring an analysis result for the pathology image from the machine learning model, and outputting the generated analysis result, in which the machine learning model may be a model trained by using a training data set generated based on a first pathology data set associated with a first domain and a second pathology data set associated with a second domain different from the first domain.

According to some examples of the present disclosure, the machine learning model is trained based on the training data set including heterogeneous domains, and as a result, the machine learning model can accurately analyse even various types of pathology images that are not used for training.

According to some examples of the present disclosure, sampling is performed on heterogeneous pathology data sets such that the machine learning model can be trained in a balanced manner without being biased toward a specific type of pathology data set.

According to some examples of the present disclosure, items included in the heterogeneous pathology data set are associated with each other, and a training data set may be generated based on the heterogeneous pathology data set with the items associated with each other. If this training data set is used for training the machine learning model, the machine learning model can perform accurate analysis of pathology images including new cancer types or cells expressed according to a new IHC staining method without performing separate training.

According to some examples of the present disclosure, by inputting training data with intentionally modified pathology images into the machine learning model and training the machine learning model, it is possible to build a machine learning model that is robust even in unintended situations such as image distortion or change.

According to some examples of the present disclosure, an analysis result including various types of output values can be output through the machine learning model. Accordingly, the user can perform follow-up procedures such as medical treatment, using a desired type of output value among the output values included in the analysis result.

The effects of the present disclosure are not limited to the effects described above, and other effects not described herein can be clearly understood by those of ordinary skill in the art (referred to as "ordinary technician") from the description of the claims.

BRIEF DESCRIPTION OF THE DRAWINGS

The above and other objects, features and advantages of the present disclosure will be described with reference to the accompanying drawings described below, where similar reference numerals indicate similar elements, but not limited thereto, in which.

DETAILED DESCRIPTION

Figure 1:
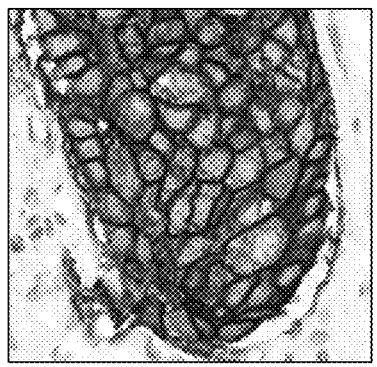
FIGS. 1 and 2 illustrate different types of pathology images.
Figure 1:
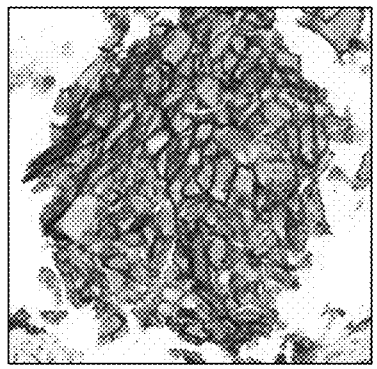

Hereinafter, example details for the practice of the present disclosure will be described in detail with reference to the accompanying drawings. However, in the following description, detailed descriptions of well-known functions or configurations will be omitted if it may make the subject matter of the present disclosure rather unclear.

In the accompanying drawings, the same or corresponding components are assigned the same reference numerals. In addition, in the following description of various examples, duplicate descriptions of the same or corresponding components may be omitted. However, even if descriptions of components are omitted, it is not intended that such components are not included in any example.

Advantages and features of the disclosed examples and methods of accomplishing the same will be apparent by referring to examples described below in connection with the accompanying drawings. However, the present disclosure is not limited to the examples disclosed below, and may be implemented in various forms different from each other, and the examples are merely provided to make the present disclosure complete, and to fully disclose the scope of the disclosure to those skilled in the art to which the present disclosure pertains.

The terms used herein will be briefly described prior to describing the disclosed example(s) in detail. The terms used herein have been selected as general terms which are widely used at present in consideration of the functions of the present disclosure, and this may be altered according to the intent of an operator skilled in the art, related practice, or introduction of new technology. In addition, in specific cases, certain terms may be arbitrarily selected by the applicant, and the meaning of the terms will be described in detail in a corresponding description of the example(s). Therefore, the terms used in the present disclosure should be defined based on the meaning of the terms and the overall content of the present disclosure rather than a simple name of each of the terms.

As used herein, the singular forms "a," "an," and "the" are intended to include the plural forms as well, unless the context clearly indicates the singular forms. Further, the plural forms are intended to include the singular forms as well, unless the context clearly indicates the plural forms. Further, throughout the description, if a portion is stated as "comprising (including)" a component, it is intended as meaning that the portion may additionally comprise (or include or have) another component, rather than excluding the same, unless specified to the contrary.

In the present disclosure, a "system" may refer to at least one of a server device and a cloud device, but is not limited thereto. For example, the system may include one or more server devices. In another example, the system may include one or more cloud devices. In still another example, the system may include both the server device and the cloud device operated in conjunction with each other.

In addition, terms such as first, second, A, B, (a), (b), etc. used in the following examples are only used to distinguish certain components from other components, and the nature, sequence, order, etc. of the components are not limited by the terms.

In addition, in the following examples, if a certain component is stated as being "connected," "combined" or "coupled" to another component, it is to be understood that there may be yet another intervening component "connected," "combined" or "coupled" between the two components, although the two components may also be directly connected or coupled to each other.

In addition, as used in the following examples, "comprise" and/or "comprising" does not foreclose the presence or addition of one or more other elements, steps, operations, and/or devices in addition to the recited elements, steps, operations, or devices.

Before describing various examples of the present disclosure, terms used will be described.

In the present disclosure, "immunohistochemistry (IHC) staining" may refer to a staining method utilizing the principle of reacting an antibody of interest on the tissue so as to observe the presence or absence of proteins (or antigens)

present in the nucleus, cytoplasm, or cell membrane in tissue or cell specimens with an optical microscope. Since the antigen-antibody reaction cannot be observed under the microscope as is, it is observed using a method of attaching a biomarker and developing the marker, and a variety of coloring agents such as red-colored AEC (3-amino-9-ethyl-carbazole) and brown-colored DAB (3,3'-diaminobenzidine) may be used.

In the present disclosure, a "pathology image" may refer to an image obtained by capturing a pathology slide that was fixed and stained through a series of chemical processing processes to observe tissue removed from the human body under the microscope. The pathology image may refer to a whole slide image (WSI) including a high-resolution image of the pathology slide, or to a part of the high-resolution whole slide image. By the part of the whole slide image, it may refer to a region divided from the whole pathology slide image based on units of a certain size. For example, the pathology image may refer to a digital image obtained by scanning a pathology slide with a digital scanner, and may include information on cells, tissues, and/or structures within the human body. In addition, the pathology image may include one or more patches, and histological components may be applied (e.g., tagged) to one or more patches through an annotation process. In the present disclosure, the "pathology image" may refer to "at least some regions included in the pathology image."

In this disclosure, the "patch" may refer to some regions in the pathology image. For example, the patch may include a region corresponding to a semantic object extracted by performing segmentation on the pathology image. As another example, the patch may refer to a combination of pixels associated with histological components generated by analysing the pathology image. For example, the patch may include an object associated with tumor tissue, an object associated with precancerous tissue, an object associated with tissue surrounding the tumor, and an object associated with other tissues.

In the present disclosure, the "histological components" may include characteristics or information on cells, tissues, and/or structures within the human body included in the pathology image. The characteristics of the cell may include cytologic feature such as nucleus and cell membrane. The histological components may refer to histological components on the patch, which may be inferred through a machine learning model or input by a pathologist.

In the present disclosure, "pathology data" may refer to pathology images including annotation information. A set of pathology data including a plurality of pathology data may be referred to as a "pathology data set." When generating a pathology data set, a domain of the pathology data may be considered. The pathology data set may be formed by collecting only the pathology images with matching domains.

In the present disclosure, the "annotation information" may be information input by an expert such as a pathologist in association with the pathology images. The annotation information may include the histological components on the pathology image. In addition, the annotation information may include at least one item associated with the pathology image. The "item" associated with the pathology image is data representing detailed information on the pathology image, and may include a first item associated with a region of the object in which staining expressed (e.g., pixel range included in the region, location of the pixel, etc.), and a second item associated with a class of the object. The object may be associated with a pixel range as a meaningful cell region (e.g., an abnormal region), and the object class may include cell type, evaluation index, etc. The cell type may be a tumor cell, a lymphocyte, etc., and the evaluation index is an index associated with the intensity of staining expression and may include positive or negative, expression grade, expression value, expression statistical information, etc. The expression grade may be a grade of cells based on staining intensity among a plurality of predetermined grades (e.g., 0, t+1, t+2, and t+3), and the expression value may be the expression value of the cell in a predetermined numerical range (e.g., 0 to 1) based on the staining intensity. In addition, the expression statistical information is statistics on the expression intensity of cells and may be output when a plurality of pathology images are analysed sequentially. For example, by analysing 10 pathology images, it is possible to calculate a ratio of PD-L1 positive tumor cells to all tumor cells in each pathology image, and the distribution of the calculated ratio values may be included in the expression statistical information. As another example, the expression statistical information may include statistical information for specific cells in a single pathology image. For example, one pathology image may be analysed, and the ratio of cells classified as specific grade cells to all cells expressing staining in the pathology image may be included in the expression statistical information.

In the present disclosure, "heterogeneous" may refer to pathology data or pathology images with different domains. When "domains" match, it may be understood that the types of the pathology images are the same as each other and the item types associated with the pathology images are consistent with each other, and when "domains" are different, it may be understood that the types of pathology images are different from each other, or the types of items associated with the pathology images are different from each other. The same type of pathology images may be understood as those having the same staining method. For example, pathology images of lung cancer tissue stained using programmed cell death ligand 1 (PD-L1) IHC staining may form a first pathology data set associated with the first domain. As another example, pathology images of breast cancer tissue stained using human epidermal growth factor receptor 2 (HER2) staining may form a second pathology data set associated with the second domain. In this case, the pathology images included in the first pathology data set and the pathology images included in the second pathology data set may be referred to as being heterogeneous. That is, if pathology data with the same domain is referred to as the same type of data, pathology data with different domains may be referred to as heterogeneous data.

In the present disclosure, "each of a plurality of A" may refer to each of all components included in the plurality of A, or may refer to each of some of the components included in a plurality of A.

In the present disclosure, "instructions" may refer to one or more instructions grouped based on functions, which are the components of a computer program and executed by the processor.

Hereinafter, various examples of the present disclosure will be described in detail with reference to the accompanying drawings.

First, various examples of pathology images that may be used for training in the present disclosure will be described with reference to FIGS. 1 to 4.

Figure 2:
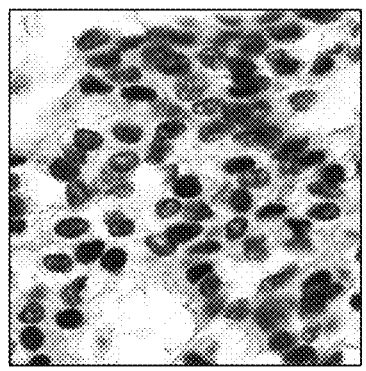
Figure 2:
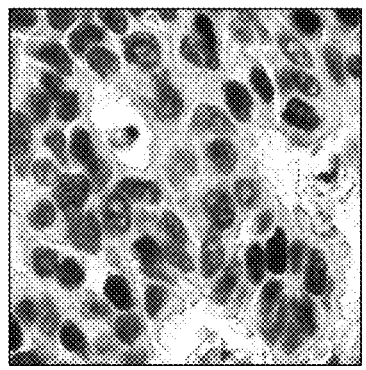

FIGS. 1 and 2 illustrate different types of pathology images. In FIG. 1, a first pathology image 110 is a slide image stained for programmed cell death ligand 1 (PD-L1) in non-small cell lung cancer using 22C3 IHC staining. In addition, a second pathology image 120 of FIG. 2 is a slide image stained for human epidermal growth factor receptor 2 (HER2) in breast cancer using HER2 IHC staining. It can be seen that while 22C3 IHC staining method and HER2 staining method utilize different antigen-antibody reactions, these staining methods have similar patterns in that the cell membranes of tumor cells have the same color (e.g., brown) after staining.

In FIG. 2, a third pathology image 210 is a breast cancer slide image stained with estrogen receptor (ER) IHC staining, and a fourth pathology image 220 is a breast cancer slide image stained with progesterone receptor (PR) IHC staining. The nuclei stained with ER IHC staining and PR IHC staining both have similar IHC staining pattern in that they have the same color (e.g., brown).

After IHC staining, heterogeneous pathology images expressing the same or similar color (e.g., brown) may be used to generate training data, which will be described below. To elaborate, a training data set may be generated based on the heterogeneous pathology data including various types of pathology images such as those illustrated in FIGS. 1 and 2, and a machine learning model may be trained using the training data set. The training data set may be a plurality of training data sets. In addition, pathology images expressing various colors (e.g., red, pink, blue, etc.) other than a specific color may be used for generating training data.

Each pathology image may include annotation information input by a pathologist. The annotation information may include at least one item about an object (e.g., cell, tissue, structure, etc.) on the pathology image. The item may include a type of an object expressing the staining input by the pathologist and a class of the object. The type of object expressing the staining on the patch and the class of the object may be referred to as labeling information for the patch. In the present disclosure, labeling information may be used interchangeably with the annotation information.

Figure 3:
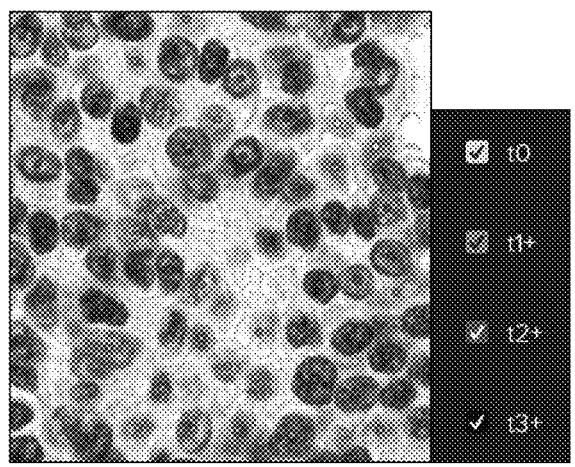
FIG. 3 illustrates a pathology image including an object class.

FIG. 3 illustrates a pathology image 310 including an object class. The pathology image 310 illustrated in FIG. 3 includes an object expressed in specific colors and object classes. A region associated with the object may be identified based on pixels expressed in the specific colors.

The object class may be determined based on an expression degree of cells in a specific color, and each class of the object may be determined according to the saturation of the specific colors. In the related art, the determination may be made by a pathologist. In other words, after checking the pathology image, the pathologist may input the class of each cell according to the degree of staining expression, and the class of the cell and the region (i.e., pixel range) of the cell set as described above may be included in the pathology image as the annotation information. FIG. 3 illustrates that the intensity of staining expression increases from t0 to t3+.

Alternatively, the object class and the object may be automatically determined using an image analysis algorithm (e.g., a machine learning model for image analysis) prepared in advance.

Figure 4:
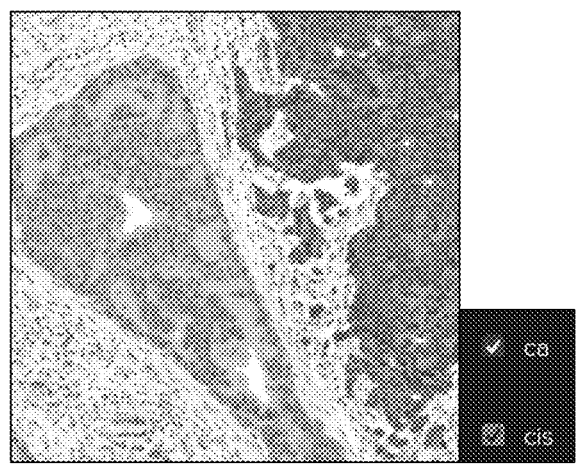
FIG. 4 illustrates a pathology image in which a tumor region and a precancerous region are segmented.

FIG. 4 illustrates a pathology image 410 in which a tumor region and a precancerous region are segmented. In the pathology image 410 illustrated in FIG. 4, a tumor region (ca) and a non-tumor region (cis) may be segmented, a tumor region (ca) may be visualized in a first color and a precancerous region (cis) may be visualized in a second color. In the related art, dividing the regions may be determined by a pathologist. For example, the pathologist could identify a tumor region (ca) and a precancerous region (cis) based on the morphological characteristics of cells and tissues expressed in the pathology image 410.

Meanwhile, this segmentation task may be performed automatically using an image analysis algorithm (e.g., a machine learning model for image analysis) prepared in advance. For example, through the image analysis algorithm, the degree of staining expression of the cells may be extracted from the pathology image, and each region may be automatically segmented based on the intensity of staining expression and visualized in different colors.

According to the type of pathology image, more regions may be segmented and visualized. For example, in the pathology image, in addition to the tumor region and precancerous region, a region surrounding the tumor (cancer stroma, etc.) may be visualized in a third color, and other tissues (connective tissue, fat tissue, bone, etc.) may be visualized in a fourth color. The annotation information associated with the visualization task may be included in the pathology image. That is, the annotation information including information on a first item associated with the visualized object region and information on a second item associated with the class of the object may be included in the pathology image.

As described above, the pathology images may be different, and the items of the annotation information included in the pathology images may also be different. The difference in the pathology images may be understood as the difference in the staining methods for the pathology images, and the difference in the body parts from which the cells are collected. For example, if a first pathology image is an image acquired through ER IHC staining and a second pathology image is an image acquired through PR IHC staining, the first pathology image and the second pathology image may be heterogeneous images. As another example, if a third pathology image is an image acquired from breast tissue and a fourth pathology image is pathology images acquired from lung tissue, the third pathology image and the fourth pathology image may be heterogeneous images.

In addition, the difference in the annotation information may be understood as the difference in the types of items included in the annotation information. For example, if the first pathology image includes a third item associated with the presence or absence of a benign condition as an object class, and the second pathology image includes a fourth item indicating a grade for any one of t0, t1+, t2+, and t3+ as the object class, the first pathology image and the second pathology image may be understood as being heterogeneous.

As described above, a pathology image that is different in any one of the type of the pathology image or the item included in the annotation information, may be determined to be a heterogeneous pathology image. The pathology images of the same type may be gathered together to form a set of pathology images of the same domain.

Hereinafter, various examples of the present disclosure will be described with reference to FIGS. 5 to 21.

Figure 5:
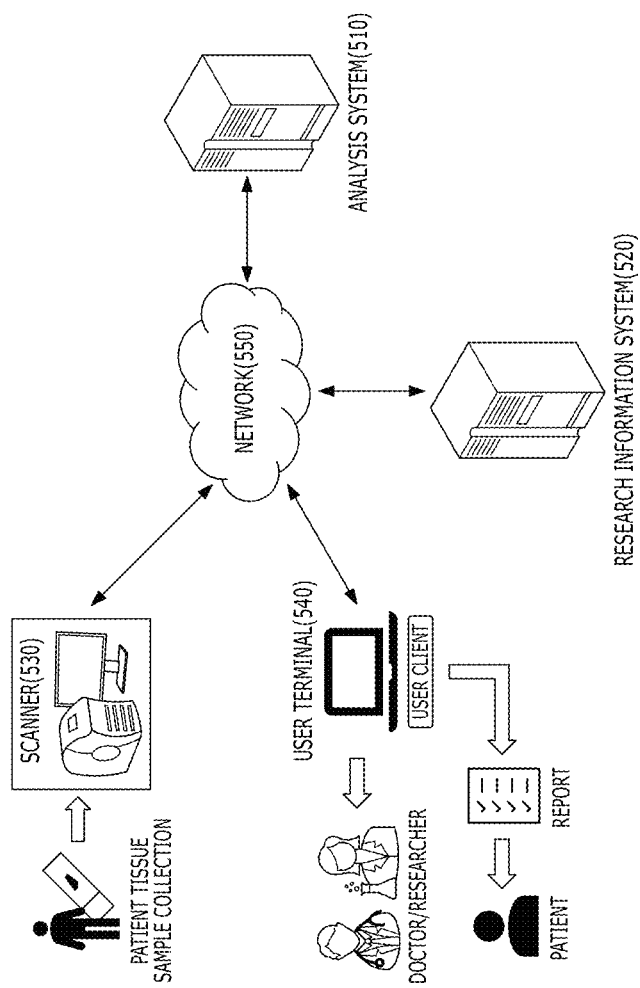
FIG. 5 illustrates an environment in which a system for analysing pathology images is applied.

FIG. 5 illustrates an environment in which a system 510 for analysing pathology images is applied. Referring to FIG. 5, the analysis system 510 may communicate with each of a research information system 520, a scanner 530, and a user terminal 540 through a network 550. The network 550 includes a mobile communication network and a wired communication network, which will not be described in detail herein as they correspond to a well-known and common technology in the technical field of the present disclosure. In addition, although not illustrated in FIG. 5, the analysis system 510 may communicate with an image management system (not illustrated) that includes a storage for storing pathology images and a storage for storing analysis results.

The scanner 530 may acquire a digitized pathology image from a tissue sample slide generated using a tissue sample of a patient. For example, the scanner 530 may generate and store pathology images which are the scanned digital images of the pathology slide. The scanner 530 may transmit the acquired pathology image from the analysis system 510.

The user terminal 540 may receive analysis result for the pathology image from the analysis system 510. For example, the user terminal 540 may be a computing device located in a medical facility such as a hospital and used by medical staff. As another example, the user terminal 540 may be a computing device used by general users such as patients.

The research information system 520 may be a computing system including servers, databases, etc. used in hospitals, universities, research facilities, etc. The research information system 520 may provide the analysis system 510 with a pathology images set which is a set of raw data used for training. For example, the research information system 520 may transmit a heterogeneous pathology data set corresponding to a single domain to the analysis system 510. As another example, the research information system 520 may provide a heterogeneous pathology data set to the analysis system 510. That is, the research information system 520 may transmit, to the analysis system 510, two or more of a first pathology data set corresponding to the first domain, a second pathology data set corresponding to the second domain, or a third pathology data set corresponding to the third domain.

The analysis system 510 includes a data storage (e.g., database) for storing a plurality of pathology data sets used for training, and may include a machine learning model for analysing pathology images. The analysis system 510 may include at least one processor and a memory. The analysis system 510 may generate a training data set based on a heterogeneous pathology data set and use the training data set to train a machine learning model. If the amount of learning of the machine learning model reaches the target amount, the analysis system 510 may perform analysis on the pathology image that does not include the annotation information using the machine learning model. That is, the analysis system 510 may perform analysis on pathology images using the machine learning model without requiring the intervention of a pathology expert. For example, the analysis system 510 may analyse the pathology image received from the scanner 530 and provide the analysed result to the client. In this case, the client may be a doctor/researcher/patient using the user terminal 540.

Hereinafter, the process of training a machine learning model will be described in more detail with reference to FIGS. 6 to 8.

Figure 6:
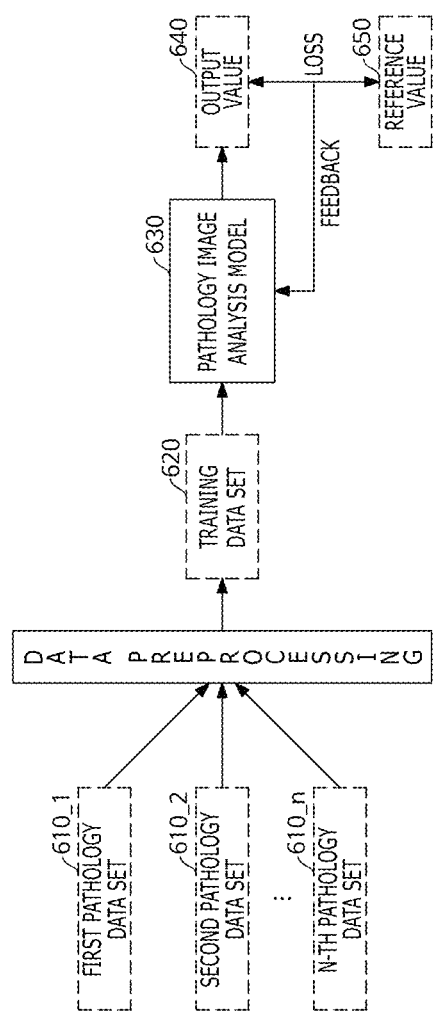
FIG. 6 is a schematic diagram illustrating training a pathology image analysis model.

FIG. 6 is a schematic diagram illustrating training a pathology image analysis model 630. In FIG. 6, a machine learning model 630 is illustrated as a pathology image analysis model 630. Hereinafter, the machine learning model 630 and the pathology image analysis model 630 will be used interchangeably.

A plurality of heterogeneous pathology data sets 610_1 to 610_*n* may be preprocessed to generate a training data set 620. That is, a plurality of heterogeneous pathology data sets 610_1 to 610_*n* corresponding to different domains may be preprocessed to generate the training data set 620 including a plurality of training data. In the process of preprocessing the heterogeneous pathology data sets 610_1 to 610_*n*, the number of samplings to be extracted from each of the pathology data sets 610_1 to 610_*n* may be determined. Data sampling will be described in detail with reference to FIG. 8.

In order to facilitate analysing the pathology images including artifacts, a robust machine learning model may be built such that intentionally distorted pathology images may be input to the pathology image analysis model 630, and analysis result may be output even for the pathology images including artifacts. In this case, the pathology image including artifacts may be an image in which some regions are distorted, converted, or removed. Various examples of generating training data in order to build a robust machine learning model will be described in detail with reference to FIG. 8.

Based on at least one of the object class or the region of interest, items associated with pathology images included in the pathology data sets 610_1 to 610_*n* may be associated with items associated with pathology images included in other pathology data sets. By the item associated with pathology images, it may mean a reference for distinguishing the type or class of cells, tissues, or structures that are present on the pathology image. For example, the first pathology data set 610_1 may include a first pathology image of a first type and the second pathology data set 610_2 may include a second pathology image of a second type, and if the first item associated with the first pathology image and the second item associated with the second pathology image correspond to a similar staining expression grade or a similar region of interest, the first item and the second item may be associated with each other. The region of interest may be a region associated with the cells. For example, the region of interest may be a region associated with at least one of tumor cells, inflammatory cells, or other cells. As another example, the region of interest may be a region associated with at least one of tumor tissue, precancerous tissue, peri-tumor tissue, or other tissues. Various examples of the associated items will be described in more detail with reference to FIG. 8, and Tables 1 and 2.

The training data set 620 including associated items may be generated. For example, if the first item associated with the first pathology image and the second item associated with the second pathology image are associated with each other, first training data may be generated based on the first pathology image and the first and second items associated with each other, and included in the training data set 620. In addition, the second training data may be generated based on the second pathology image and the first and second items associated with each other, and included in the training data set 620. Accordingly, the training data set 620 may further include items of heterogeneous pathology images associated with items included in the pathology images, in addition to the pathology images.

At least one batch including part or all of the training data set 620 may be generated and the pathology image analysis model 630 may be trained. During the training process, a loss value between an output value (i.e., analysis result) 640 output from the pathology image analysis model 630 and a reference value 650 may be calculated. The reference value 650 may be a type of correct value acquired from the annotation information of the pathology images. For example, the reference value 650 may be acquired from the evaluation index included in the annotation information.

The loss value may be fed back to the pathology image analysis model 630 and the weight of at least one node included in the pathology image analysis model 630 may be adjusted. The node may be a node included in an artificial neural network.

According to examples of the present disclosure, if training data is input to the pathology image analysis model 630, the associated items included in the training data may be grouped into similar item groups and may operate as at least one node having a weight in the pathology image analysis model 630. If the pathology image analysis model 630 is trained by inputting these associated items together, it is possible to not only perform analysis on various types of pathology images, but also output various types of result values.

Hereinafter, a method by which the pathology image analysis model is trained will be described in detail with reference to FIGS. 7 and 8. The method shown in FIGS. 7 and 8 is merely an example for achieving the purpose of the present disclosure, and it goes without saying that some steps may be added or deleted as needed. In addition, the method illustrated in FIGS. 7 and 8 may be performed by at least one processor included in the analysis system illustrated in FIG. 5. For convenience of explanation, it will be described that each step illustrated in FIGS. 7 and 8 is performed by the processor included in the analysis system illustrated in FIG. 5.

In addition, in the examples described below, it is assumed that the heterogeneous pathology data set includes a plurality of heterogeneous pathology data sets of different types. In addition, in the description described below, N-th (where N is a natural number) heterogeneous pathology data set and N+1-th heterogeneous pathology data set are referred to as the data sets corresponding to different domains.

Figure 7:
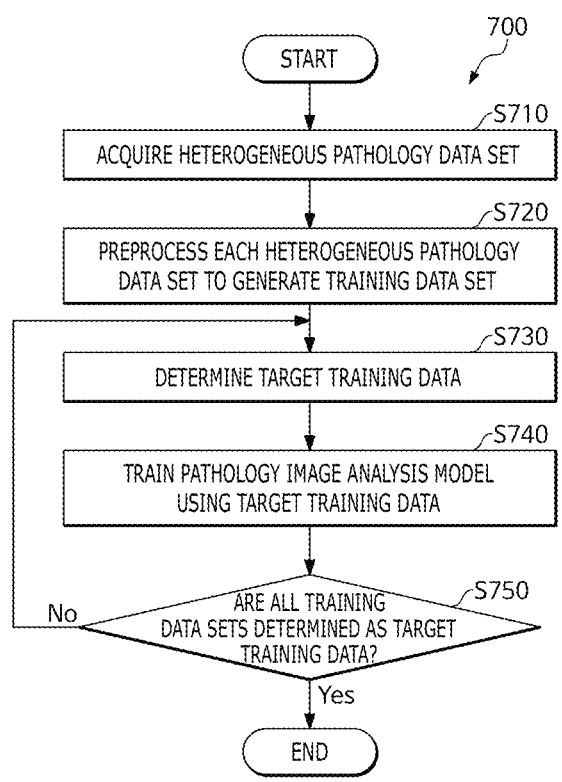
FIG. 7 is a flowchart illustrating a method for training a pathology image analysis model.

FIG. 7 is a flowchart illustrating a method 700 for training a pathology image analysis model. Referring to FIG. 7, the processor may acquire a heterogeneous pathology data set, at S710. For example, the processor may acquire, from a storage, the heterogeneous pathology data set received from at least one of the analysis system 510, the research information system 520, or the scanner 530 of FIG. 5 and stored.

The processor may preprocess each of the acquired heterogeneous pathology data sets to generate a training data set, at S720. The individual training data may include pathology images including annotation information. The processor may associate an item associated with the first pathology image with an item associated with the second pathology image, and cause the associated items to be included in each pathology data set. Accordingly, the heterogeneous individual pathology data included in the heterogeneous pathology data set may be merged with each other. The processor may determine the number of training data and generate the training data set to have a number of data corresponding to this number, so that the size of the training data set corresponds to the predetermined batch size. According to some examples, the processor may perform at least one of sampling or data augmentation on the heterogeneous pathology data set. A more detailed description of data preprocessing will be described below with reference to FIGS. 8 to 10.

If the data preprocessing is completed, the processor may determine target training data from among the data included in the training data set, at S730. The processor may train the pathology image analysis model using the target training data, at S740. The processor may determine a reference value from the annotation information included in the target training data. For example, the processor may extract an object class from the annotation information included in the training data and determine a reference value based on the evaluation index included in the extracted object class. In addition, the processor may determine a reference value based on the region (i.e., pixel range) of at least one segmented object and the type (i.e., cell type) of each object from the annotation information included in the training data.

The processor may input the target training data into the pathology image analysis model, calculate a loss value between an output value (i.e., analysis result) output from the pathology image analysis model and the reference value, and feed back the calculated loss value to the pathology image analysis model, thereby adjusting at least one weight included in the pathology image analysis model. The output value may include an evaluation index or at least one of the object region and the object type (i.e., cell type). The loss value may be calculated by mathematically calculating a difference between the evaluation index and the reference value, or may be calculated by using an evaluation function to evaluate a pixel range matching rate between the object included in the output value and the object included in the reference value.

The processor may determine whether all data included in the training data set is determined as the target training data, at S750. If there is data in the training data set which is not yet determined as the target training data, the processor may determine, as the target training data, one of the training data that is not determined as the target training data, and train the pathology image analysis model by using this target training data.

Meanwhile, if all data included in the training data set is determined as the target training data, the processor may end training at the epoch of this cycle.

Meanwhile, in the epoch of the next cycle, the same training data set may be used again to train the pathology image analysis model again, or a new training data set may be generated and the pathology image analysis model may be trained again.

As described above, as training the pathology image analysis model using the data included in the training data set repeats, the weight of each node included in the pathology image analysis model may converge to an optimal value. Accordingly, the pathology image analysis model may output more accurate analysis result.

Figure 8:
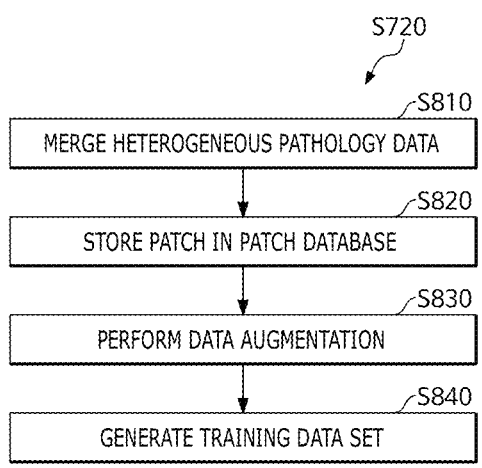
FIG. 8 is a flowchart illustrating a method for preprocessing a heterogeneous pathology data set to generate a training data set.

FIG. 8 is a flowchart illustrating a method for preprocessing a heterogeneous pathology data set to generate a training data set. Prior to describing the method for data preprocessing, the reason for requiring preprocessing will be briefly described.

The first pathology image and the second pathology image, which are heterogeneous pathology images, may differ from each other in at least one of cell type, staining intensity, or tissue region required for IHC evaluation. Most pathology images have in common that these images include information of labeled tumor cells, but in certain cases, depending on the IHC type, in addition to tumor cells, immune cells such as lymphocytes and macrophages, and stromal cells such as fibroblasts and adipocytes that make up the stroma around the tumor may also be stained, and labeling information for these cells may be included in some types of heterogeneous images. To elaborate, a training data set including various types of pathology images such as those illustrated in FIGS. 1 to 4 may be generated, and the machine learning model may be trained based on the training data set.

In addition, the reference for evaluating staining intensity may also differ depending on the cell type (e.g., cancer type) forming the pathology image and the type of IHC. For example, in the case of the IHC dataset evaluating the degree of HER2 expression in breast cancer, the degree of HER2 expression in tumor cells is classified into four levels: 3+

(strong), 2+ (medium), 1+ (weak), and 0 (no expression), but in the case of IHC datasets evaluating the degree of PD-L1 expression in lung cancer using 22C3 staining, the degree of PD-L1 expression in tumor cells is classified as positive or negative.

Since the types of labeled cells, evaluation indices for staining intensity, etc. may differ depending on the type of pathology image, there is a need to build a training data set by merging different types of items. In other words, there is a need to build an integrated training data set by performing domain merging on pathology images from different domains. For example, if the types of the first object class in the first pathology image and the second object class in the second pathology image are different from each other, the first object class and the second object class may be integrated. Meanwhile, an object class in a particular pathology data set may have more or less sub items than others, and the items may be associated such that the items are merged to have more or less sub items. If the items are merged to have less sub items, a method for grouping a plurality of cell types or staining intensities into one may be used, as illustrated in the examples in Tables 1 and 2 below.

If data is integrated to have more sub items, the evaluation is performed again on the pathology image with fewer labeled sub items, so that a larger number of sub items can be labeled in the pathology image. In this case, a separate algorithm (e.g., a machine learning model) that automatically labels sub items may be used, so that pathology images labeled with a smaller number of sub items may be automatically re-labeled with a larger number of sub items. For example, if the number of sub items associated with the object class of the first pathology image is 2 and the number of sub items associated with the object class of the second pathology image is 4, an algorithm (e.g., a machine learning model) that automatically labels the first pathology image with four sub items may be input, and the first pathology image labeled with the four sub items may be output through this algorithm.

This association of items is based on the pathological theory that even if the tumor cells of interest in IHC analysis are different cancer types, tumor cells of interest in IHC analysis have similar morphologic feature such as nuclear atypia, high nuclear/cytoplasmic ratio, increased atypical mitosis, and loss of polarity that are common to all malignant tumor cells regardless of their origin and that immune cells, stromal cells, etc. have little difference in shape according to the cancer type.

Referring to FIG. 8, the processor may merge heterogeneous pathology data sets corresponding to heterogeneous domains by processing different items included in the heterogeneous pathology data sets to be associated with each other, at S810. By "merging," it may mean that heterogeneous pathology data sets are associated with each other with common items.

A table of items that may be associated with each other may be stored in the analysis system in advance, and the processor may refer to the table to extract the items that are associated with each other from the heterogeneous pathology data set and process the extracted items to be associated with each other. Tables 1 and 2 below illustrate mapping tables that are referenced when associating items. For example, Tables 1 and 2 map the items using the first pathology data set associated with PD-L1 and the second pathology data set associated with HER2. That is, the mapping tables are illustrated, which are used for associating items associated with a first type of pathology image using PD-L1 IHC staining, with items associated with a second type of pathology image using HER2 IHC staining.

TABLE 1

| | Tissue mapping | |
|---|---|---|
| | BG (Background) | CA (Cancer region) |
| PD-L1 lung | BG | CA |
| HER2 breast | BG, CIS | CA |

TABLE 2

| | Cell mapping | | |
|---|---|---|---|
| | Other Cell | TC− | TC+ |
| PD-L1 lung | LP+, LP−, MP+, MP−, OT | TC− | TC+ |
| HER2 breast | OT | TC0 | TC1, TC2, TC3 |

Referring to Tables 1 and 2, the first type of pathology image associated with PD-L1 IHC staining and the second type of pathology image associated with HER2 IHC staining have different staining methods and primary sites (lung or breast), but these images have one thing in common that they are expressed in characteristic colors. Meanwhile, although objects associated with cancer type may be commonly found in the first pathology image and the second pathology image, the type of expressed cells, staining intensities, and tissue regions required for IHC evaluation may be different. In the present disclosure, among items associated with heterogeneous pathology images, items having properties in common may be associated. Table 1 illustrates that items associated with the heterogeneous pathology images may be associated with each other based on the tissue of interest. Referring to Table 1, an item CA representing tumor tissue of the items associated with the first type of pathology image acquired with PD-L1 IHC staining may be associated with an item CA representing tumor tissue of the items associated with the second type of pathology image acquired with HER2 IHC staining. In addition, an object-related item BG representing non-tumor tissue of the items associated with the first type of pathology image acquired with PD-L1 IHC staining may be related to precancerous tissue CIS and background tissue BG of items associated with the second type of pathology image acquired with HER2 IHC staining.

Table 2 illustrates that items associated with the heterogeneous pathology images may be associated with each other based on the object class. Referring to Table 2, lymphocytes (LP+, LP−), macrophages (MP+, MP−) and other cells (OT), excluding tumors, of the items associated with the first type of pathology image acquired with PD-L1 IHC staining may be associated with cells other than tumor (BG) and precancerous tissue (CIS) (OT) of the items associated with the second type of pathology image acquired with HER2 IHC staining.

In addition, a negative item (TC−) related to the first expression range of the items indicating the intensity of each staining expression of pixels included in the first type of pathology image may be associated with an item TC0 related to the first expression range of items indicating the intensity of each staining expression of pixels included in the second type of pathology image. In addition, a positive item (TC+) related to the second expression range of the items indicating the intensity of each staining expression of pixels included in the first type of pathology image may be associated with items TC1, TC2, and TC3 related to the second expression range of items indicating the intensity of each staining expression of pixels included in the second type of pathology image.

The processor may associate an item associated with the first pathology image with an item associated with the second pathology image, and cause the associated items to be included in each pathology data set. Accordingly, the heterogeneous individual pathology data included in the heterogeneous pathology data set may be merged with each other.

Taking Tables 1 and 2 as an example, the BG item associated with the first pathology image, and the BG item and CIS item associated with the second image may be associated. In addition, the item OT associated with the second pathology image may be associated with the items LP+, LP−, MP+, MP−, and OT associated with the first pathology image. In addition, the item TC− associated with the first pathology image may be associated with the item TC0 associated with the second pathology image, and the item TC+ associated with the first pathology image may be associated with items TC1, TC2, and TC3 associated with the second pathology image. These associated items may be included in each of the first pathology data set and the second pathology data set, and accordingly, the first pathology data set associated with the first domain and the second pathology data set associated with the second domain may be merged.

The processor may extract labeled patches from each pathology data set and store the extracted patches in the patch database, at S820. The labeled patch may refer to an object with labeled object class, and may be part or all of the pathology image. The processor may extract the same predetermined number of patches from each pathology data set. According to another example, the processor may extract a different number of labeled patches from each pathology data set. The processor may extract a first number or a first ratio of labeled patches from the first pathology data set and a second number or a second ratio of labeled patches from the second pathology data set.

After extracting the labeled patches, the processor may store the labeled patches in a patch database. In this case, the labeled patches may include an item (e.g., object type, class, etc.) and an item of heterogeneous pathology data associated with this item. In another example, the processor may copy a predetermined number of patches of a specific type and store the copied patches in the patch database. In this case, the predetermined number of the specific type of patches to be copied may be determined based on the patch type with the largest number of patches. For example, the number of patches to be copied may be determined based on a difference between the largest number of patch types and the number of specific type patches of the patch types stored in the patch database. The patch type may correspond to the type of pathology image. For example, if the type of pathology image is the first type, the patches extracted from the pathology image may also be the first type. Examples of the patches stored in the patch list or patch database will be described with reference to FIGS. 9 and 10.

The processor may augment the labeled patch by applying artificial modifications such as distortion, deletion, contamination, etc. to the image included in the patch database, at S830.

To generate an augmented patch, the processor may extract at least one patch from among the patches included in the patch database and adjust the size of the extracted patch. For example, the processor may change the resolution of the size of the patch to a higher or lower resolution than the original resolution. As another example, the processor may change the size of the patch by removing pixels located outside the patch.

In addition, the processor may extract at least one patch from among the patches included in the patch database and remove pixels corresponding to a predetermined range from the pixels included in the extracted patch. In addition, the processor may enlarge the size of the patch, which is removed of the pixels, to the original size of the patch. If a pathology image analysis model is trained based on images including this type of patch, the pathology image analysis model may be trained to accurately detect the region of interest and accurately calculate an evaluation index for the detected region of interest even if the region of interest is in various locations in the pathology image.

In addition, the processor may extract at least one patch from among the patches included in the patch database, invert the extracted patch left-right or upside-down, and generate a patch with the left/right or top/bottom inverted. If the pathology image analysis model is trained using the pathology images including the inverted patch, the pathology image analysis model may be trained to output meaningful analysis result even for new types of pathology images.

In addition, the processor may extract at least one patch from the patches included in the patch database and remove pixels within a predetermined range from the pixels included in the extracted patch to augment the patch. If the pathology image analysis model is trained using pathology images including the patch that is intentionally removed of the pixels, the pathology image analysis model may output accurate analysis result even for pathology images including artifacts.

In addition, the processor may extract at least one patch from the patches included in the patch database and artificially modified the pixels within a predetermined range from the pixels included in the extracted patch to augment the patch. For example, the processor may use a median-filter to apply a blurriness effect to the pixels in a determined range so that some pixels become blurred, thereby modifying the corresponding pixels. As another example, the processor may use a Gaussian-filter and add noise to the pixels in a determined range to modify some pixels. If the pathology image analysis model is trained using pathology images including the modified patch, the pathology image analysis model that is robust against scanner errors, staining errors, etc. may be built.

In addition, the processor may extract at least one patch from the patches included in the patch database, convert the colors of the pixels included in the extracted patch, and generate a patch including the converted color to augment the patch. For example, the processor may change at least one of the hue, contrast, brightness, or saturation of the patch using a color jittering technique. As another example, the processor may change the color of the patch using a grayscale technique. Detailed setting values for changing the color of a patch may be determined by the user. If the pathology image analysis model is trained using pathology images including the color-changed patch, even if pathology images of a new domain is input, the pathology image analysis model may output meaningful analysis result for the pathology image, and also induce the pathology image analysis model to be trained by focusing more on the cellular structure rather than the color of the image.

After the data augmentation is completed, the processor may generate a training data set using at least one augmented patch and some or all of the patches included in the patch database, at S840. The processor may determine the number of patches of each type used for generating a training data set, extract the determined number of patches for each type from the patch database, and generate a training data set using the extracted patches for each type and augmented patches. According to another example, the processor may randomly extract a predetermined number of patches from the patches included in the patch database regardless of type and generate training data using the extracted patches. According to another example, the processor may generate a training data set using all patches included in the patch database. If only some of the patches included in the patch database are extracted to generate a training data set, this may be referred to as a training data set corresponding to a mini-batch size.

Individual training data included in the training data set may include at least one patch. In addition, the individual training data may include different types of patches. Additionally or alternatively, the individual training data may include patches of the same type. According to some examples, the processor may generate pathology images for training a predetermined size and randomly place at least one patch on the pathology image. In addition, the processor may insert a randomly selected background image into a region other than the patch in the pathology image for training where the patch is placed. In this case, the background image may be extracted from an actually scanned pathology image, and the analysis system may store a plurality of background images in advance. In this case, the processor may randomly select one of the plurality of background images and insert the selected background image as the background of the pathology image for training.

The reason for inserting the background image as described above is to train the pathology image analysis model to perform a segmentation task from the pathology image. As described below, if the first analysis model that performs segmentation on the pathology image is included in the pathology image analysis model, pathology images for training including both the patch and the background image is input to the first analysis model, so that the first analysis model may be trained. For this segmentation training, pathology images including at least one patch and the background image may be generated.

As described above, the individual training data includes pathology images for training and may also include at least one labeled patch. In addition, individual training data may include heterogeneous items that are associated with each other.

Figure 9:
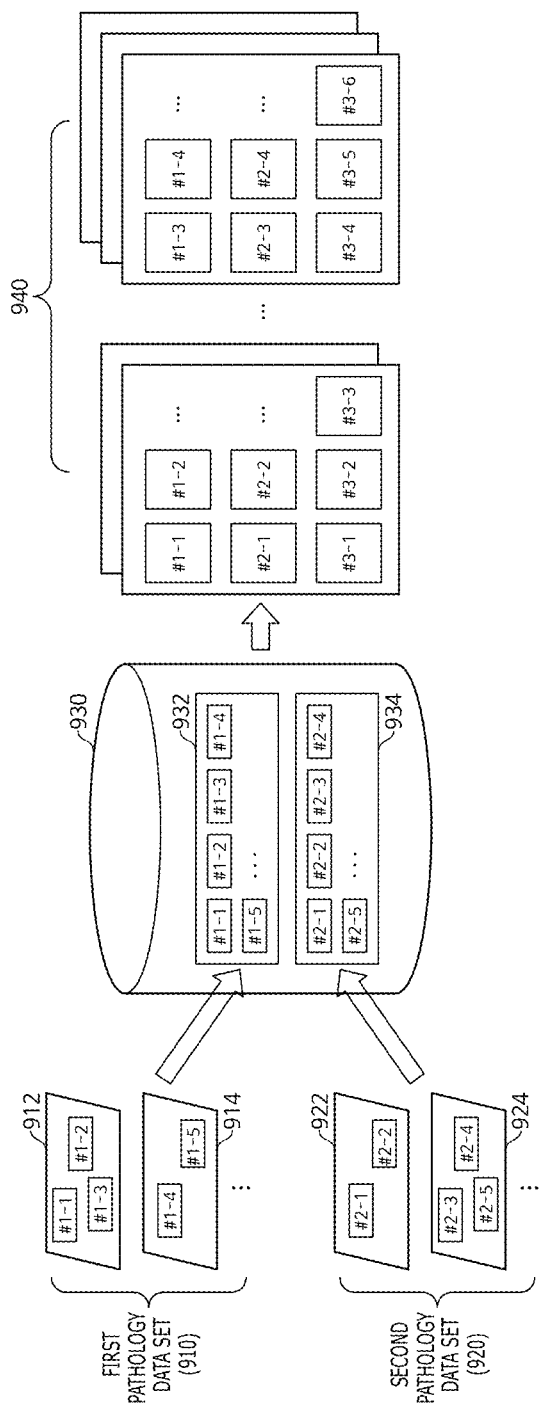
FIG. 9 illustrates an example in which patches are sampled to generate a batch.

FIG. 9 illustrates an example in which patches are sampled to generate a batch 940. Referring to FIG. 9, a first pathology data set 910 associated with the first domain may include a first type of pathology images 912 and 914, and a second pathology data set 920 associated with the second domain may include a second type of pathology images 922 and 924.

Figure 10:
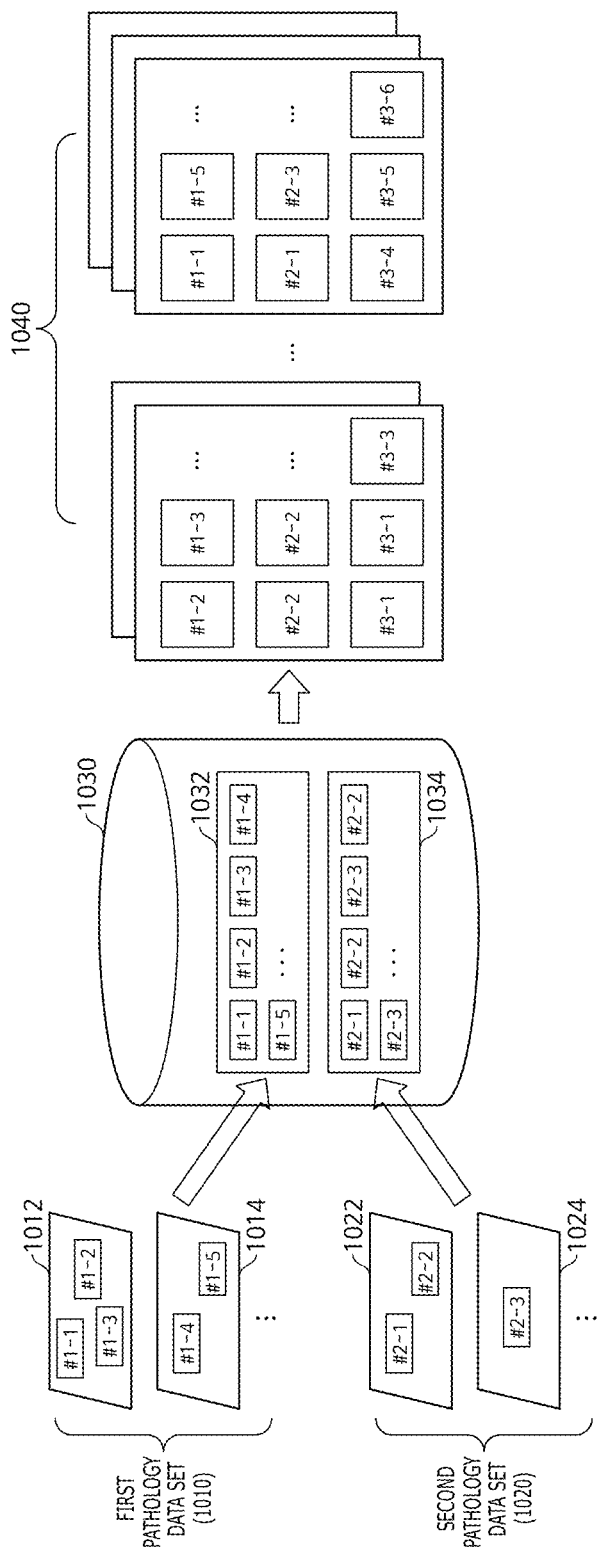
FIG. 10 illustrates another example in which patches are sampled to generate a batch.

Each pathology image may include a labeled patch. In FIG. 9, the patch is expressed as a square with a combination of "#" and a number. Although the shape of the patch in FIGS. 9 and 10 is illustrated as a square of the same size, this is merely for convenience of explanation, and in reality, the shape and size of the patch may be different in each pathology image.

As illustrated in FIG. 9, patches (#1-1 to #1-5) in the first pathology data set 910 may be extracted and stored in a patch database 930. Likewise, patches (#2-1 to #2-5) in the second pathology data set 920 may be extracted and stored in the patch database 930.

The patch database 930 may store a first type of patches (#1-1 to #1-5) 932 and a second type of patches (#2-1 to #2-5) 934. The processor may determine the number of sampling for the first type of patches 932 included in the patch database 930 and determine the number of sampling for the second type of patches 934 and fetch each type of patches corresponding to the determined numbers from the patch database 930. The number or ratio of sampling extracted from each type may be set by the user in advance. For example, the number of sampling for the first type of patch may be 100, and the number of sampling for the second type of patch may be 50.

The processor may generate the batch 940 of a predetermined size using the patches extracted from the patch database 930. The batch 940 generated in this way may form part or all of a training data set. In this case, the processor may augment the patches in the patch database 930 and generate the batch 940 including the augmented patches (#3-1 to #3-6).

FIG. 10 illustrates another example in which patches are sampled to generate a batch 1040. Referring to FIG. 10, a first pathology data set 1010 associated with the first domain may include a first type of pathology images 1012 and 1014, and a second pathology data set 1020 associated with the second domain may include a second type of pathology images 1022 and 1024.

As illustrated in FIG. 10, the patches (#1-1 to #1-5) included in the first pathology data set 1010 may be extracted and stored in a patch database 1030. Likewise, the patches (#2-1 to #2-3) included in the second pathology data set 1020 may be extracted and stored in the patch database 1030.

Meanwhile, if the number of patches (#2-1 to #2-3) extracted from the second pathology data set 1020 is less than the number of patches (#1-1 to #1-5) extracted from the first pathology data set 1010, patch copying may be performed for at least one of the patches (#2-1 to #2-3) extracted from the second pathology data set 1020. For example, patch copying may be performed for the first type of patches or the second type of patches such that equal number of first type patches and second type patches are stored in the patch database 1030. In addition, patch copying may be performed for the first type of patches or the second type of patches such that the number of first type patches and the number of second type patches are in a predetermined ratio.

FIG. 10 illustrates that patch copying is performed for patches #2-2 and #2-3. The copied patches #2-2 and #2-3 may be included in the patch database 1030. As the patch copying is performed, the number of each type of patches may be balanced and stored in the patch database 1030.

The processor may randomly fetch a predetermined number of patches 1032 and 1034 stored in the patch database 1030, and use the extracted patches to generate the batch 1040 to form part or all of the training data set. As another example, the processor may determine the number of sampling for the first type of patches 1032 included in the patch database 1030 and determine the number of sampling for the second type of patches 1034, fetch the determined number of each type of patches from the patch database 1030, and generate the batch 1040 using the fetched patches. The processor may augment the patches in the patch database 1030 to generate the batch 1040 including the augmented patches (#3-1 to #3-6).

Meanwhile, a training data set may be generated using heterogeneous pathology images including annotation information, without performing the task of extracting patches from the pathology images including annotation information. Specifically, the processor of the analysis system may generate a training data set based on a plurality of first type of pathology images extracted from the first pathology data set and a plurality of second type of pathology images extracted from the second pathology data set. In this case, the processor of the analysis system may generate a plurality of training data based on each of the extracted first type pathology images, and may generate a plurality of training data based on each of the second type of pathology images included in the second pathology data set.

The processor may extract a plurality of first type of pathology images from the first set of pathology images so as to correspond to the first number of sampling, and extract a plurality of second type of pathology images from the second pathology image set so as to correspond to the second number of sampling. In addition, the processor may augment at least one of the first pathology image and the second pathology image to generate a training data set including the augmented image. As a method for image enhancement, the image enhancement method associated with the patches described above may be used.

Meanwhile, in order to output more accurate result for a specific type of cell or a specific staining method, an additional training data set may be input to the pathology image analysis model, and the pathology image analysis model may be additionally trained to improve performance. The specific staining method may be a related staining method (e.g., H&E staining method) or a newly developed staining method. For example, an additional training data set including a plurality of pathology images stained through a specific staining method may be prepared, and this additional training data set may be used to further train the pathology image analysis model. In this case, the weights of nodes included in the pathology image analysis model may be adjusted to respond more sensitively to a specific staining method.

Figure 11:
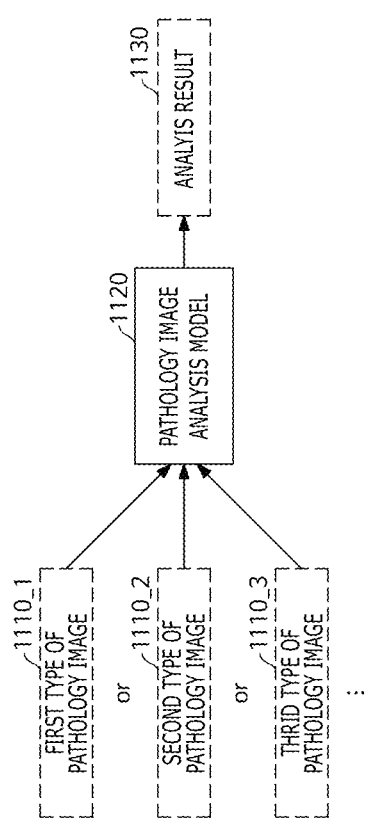
FIG. 11 illustrates a process in which an analysis result of pathology images is output through a pathology image analysis model.

FIG. 11 illustrates a process in which an analysis result of pathology images is output through a pathology image analysis model. As illustrated in FIG. 11, various types of pathology images 1110_1 to 1110_3 may be input to a pathology image analysis model 1120. The pathology images 1110_1 to 1110_3 may be of the same type as the pathology images used for training, or may be pathology images acquired through anew biomarker. That is, the domain associated with the pathology images 1110_1 to 1110_3 may be the domain same as or different from the domain trained in the pathology image analysis model 1120.

The pathology image analysis model 1120 may output an analysis result 1130 for the pathology images 1110_1 to 1110_3. The analysis result 1130 may include a class for each object extracted from the pathology images 1110_1 to 1110_3. The object class includes a cell type and/or an evaluation index, and the evaluation index may include at least one of positive or negative, expression grade, expression value, or expression statistical information. In addition, the analysis result 1130 may be a segmentation result for the pathology images 1110_1 to 1110_3. That is, the analysis result 1130 may include at least one tissue identified from the pathology images 1110_1 to 1110_3 and the type of the tissue.

Figure 12:
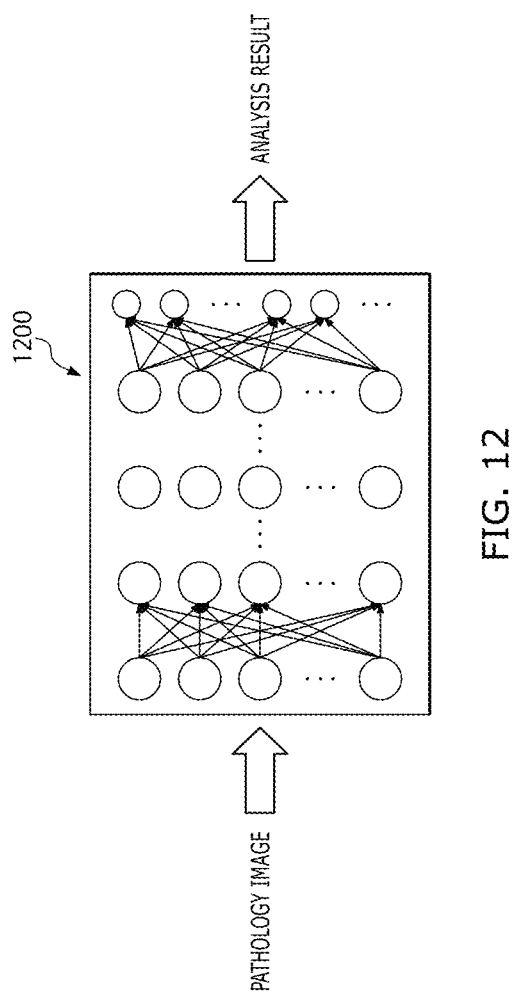
FIG. 12 illustrates an artificial neural network model included in a pathology image analysis model.

FIG. 12 illustrates an artificial neural network model 1200 included in a pathology image analysis model. In machine learning technology and cognitive science, the artificial neural network model 1200 as an example of the machine learning model refers to a statistical learning algorithm implemented based on a structure of a biological neural network, or to a structure that executes such algorithm.

The artificial neural network model 1200 may represent a machine learning model that acquires a problem solving ability by repeatedly adjusting the weights of synapses by the nodes that are artificial neurons forming the network through synaptic combinations as in the biological neural networks, thus training to reduce errors between a target output corresponding to a specific input and a deduced output. For example, the artificial neural network model 1200 may include any probability model, neural network model, and the like, that is used in artificial intelligence learning methods such as machine learning and deep learning.

The pathology image analysis model described above may be implemented in the form of the artificial neural network model 1200. The artificial neural network model 1200 may be trained to receive one or more pathology images including annotation information and detect objects expressed as staining in the one or more received pathology images. For example, the artificial neural network model 1200 may be trained to perform a classification function (i.e., a function of a classifier) for determining whether each region corresponds to a normal region or an abnormal region for each region in one or more pathology images. In another example, the artificial neural network model 1200 may be trained to perform a segmentation function that performs labeling of pixels included in abnormal regions within one or more pathology images. In this case, the artificial neural network model 1200 may determine an evaluation index for the object associated with the abnormal region and label the object.

The artificial neural network model 1200 may be implemented as a multi-layer perceptron (MLP) formed of multi-layer nodes and connections between them. The artificial neural network model 1200 may be implemented using one of various artificial neural network model structures including the MLP. The artificial neural network model 1200 includes an input layer that receives input signals or data from the outside, an output layer that outputs output signals or data corresponding to the input data, and n (where, n is a positive integer) hidden layers that are located between the input layer and the output layer, receive signals from the input layer, extract characteristics, and transmit the characteristics to the output layer.

The input layer and the output layer of the artificial neural network model 1200 are respectively matched with a plurality of output variables corresponding to a plurality of input variables, and as synaptic values between nodes included in the input layer, the hidden layers, and the output layer are adjusted, the model can be processed to extract a correct output corresponding to a specific input. If the artificial neural network model 1200 is repeatedly trained based on the data included in the training data set, the synaptic values (or weights) between the nodes of the artificial neural network model 1200 may be adjusted to reduce the error between the output variables calculated based on the input variable and the target output, and converge to an optimal value.

As described above, if a sufficient amount of training is performed on the pathology image analysis model, an analysis result corresponding to the level of pathology experts can be output through the pathology image analysis model, even for the pathology images for which annotation information is not input (i.e., unlabeled).

Figure 13:
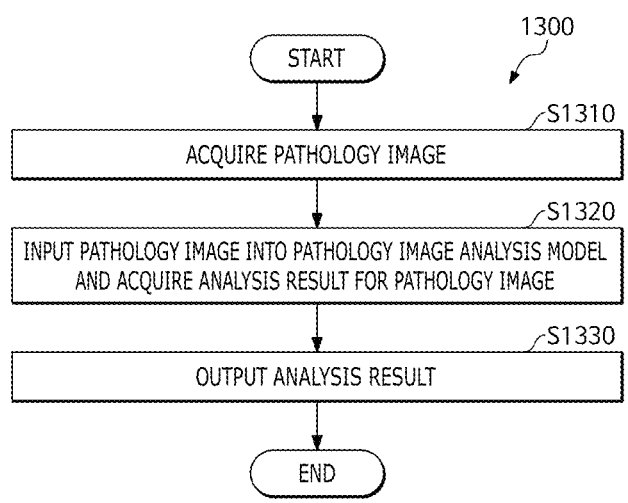
FIG. 13 is a flowchart illustrating a method for outputting an analysis result for pathology images using a pathology image analysis model.

FIG. 13 is a flowchart illustrating a method 1300 for outputting an analysis result for pathology images using a pathology image analysis model. The method illustrated in FIG. 13 is merely one example for achieving the object of the present disclosure, and it goes without saying that certain steps may be added or omitted as needed. In addition, the method illustrated in FIG. 13 may be performed by at least one processor included in the analysis system illustrated in FIG. 5. For convenience of explanation, it will be described that each step of operation illustrated in FIG. 13 is performed by a processor included in the analysis system illustrated in FIG. 5.

Referring to FIG. 13, the processor may acquire pathology images, at S1310. The processor may acquire the pathology images transmitted from a scanner, or acquire the pathology images from an external storage, a server, or an image management system.

The processor may input the pathology images into the pathology image analysis model and acquire analysis result for the pathology images output from the pathology image analysis model, at S1320. The analysis result may include an object identified from the pathology images (that is, a pixel range included within a region corresponding to the object) and an object class. The object class includes a type of cell or tissue and/or an evaluation index, and the evaluation index may include at least one of positive or negative, expression grade, expression value, or expression statistical information.

The processor may output the acquired analysis result, at S1330. For example, the processor may output the analysis result to a display device such as a monitor. As another example, the processor may transmit the analysis result to a client's terminal and output the analysis result through the client's terminal. The processor may output the acquired analysis result in the form of a report.

Meanwhile, the pathology image analysis model may include a plurality of analysis models that output different types of analysis results.

Figure 14:
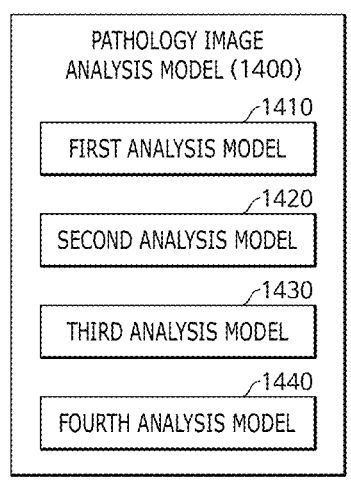
FIG. 14 illustrates a pathology image analysis model according to another example of the present disclosure.

FIG. 14 illustrates a pathology image analysis model 1400 according to another example of the present disclosure. As illustrated in FIG. 14, the pathology image analysis model 1400 may include a plurality of analysis models 1410 to 1440 that are pre-trained to analyse different types of pathology images and output different types of analysis results. For example, the pathology image analysis model 1400 may include a first analysis model 1410 that outputs a segmentation result for the input pathology images, a second analysis model 1420 that analyses the staining intensity of the cell membrane included in the pathology images and outputs an analysis result, a third analysis model 1430 that analyses the staining intensity of the cell nucleus and outputs an analysis result, and a fourth analysis model 1440 that analyses the morphological characteristics of the cell nucleus and/or cell membrane and outputs an analysis result.

If a plurality of analysis models are included in the pathology image analysis model 1400 as described above, each of the analysis models 1410 to 1440 may be trained based on a training data set including pathology images having different characteristics. The characteristic may include at least one of staining color, type of staining object, or staining method.

For example, the first analysis model 1410 may be trained to receive the target training data and segment an abnormal region (i.e., object related to patches) from the pathology images included in the target training data. That is, the first analysis model 1410 may be trained to extract the location region (i.e., object) where staining is expressed in the pathology image. In this case, the pathology images may be input to the first analysis model 1410 and at least one patch may be output from the first analysis model 1410. In addition, the loss value between the region corresponding to the patch output from the first analysis model 1410 and the abnormal region included in the annotation information may be calculated, and the loss value may be fed back to the first analysis model 1410 to train the first analysis model 1410.

As another example, the second analysis model 1420 may be trained to receive target training data including pathology images in which cell membranes are stained brown, and analyse the staining intensity of the patch included in the pathology image. In this case, the pathology images with a brown-stained cell membrane set as a patch may be input to the second analysis model 1420, and an analysis result of the staining intensity for the cell membrane may be output from the second analysis model 1420. In addition, after the evaluation index is extracted from the labeling information of the patch included in the target training data and the loss value between the evaluation index and the analysis result output from the second analysis model 1420 is calculated, the loss value may be fed back to the second analysis model 1420, thereby training the second analysis model 1420.

As another example, the third analysis model 1430 may be trained to receive target training data including pathology images in which cell nuclei are stained blue, and analyse the staining intensity of the patch included in the pathology image. In this case, pathology images with blue-stained cell nuclei set as a patch may be input to the third analysis model 1430, and an analysis result of the staining intensity for the cell nuclei may be output from the third analysis model 1430. In addition, after the evaluation index is extracted as a reference value from the labeling information of the patch included in the target training data, and the loss value between the analysis result output from the third analysis model 1430 and the evaluation index is calculated, the loss value may be fed back to the third analysis model 1430, thereby training the third analysis model 1430.

As another example, the fourth analysis model 1440 may be trained to receive target training data including pathology images in which cell nuclei and cell membranes are stained pink, and analyse the morphological characteristics of cell nuclei and/or cell membranes included in the pathology image and/or color distribution. In this case, the pathology images in which each of the cell nucleus and cell membrane stained in pink is set as a patch may be input to the fourth analysis model 1440, and an analysis result including morphological characteristics for the cell nucleus and/or cell membrane and/or color distribution may be output from the fourth analysis model 1440. In addition, the morphological characteristics of the cell nucleus and/or cell membrane and/or color distribution are acquired as reference values from the labeling information of the patch included in the target training data, and morphological characteristics and/or color distribution loss values included in the reference value and analysis result may be calculated. The calculated loss values are fed back to the fourth analysis model 1440, so that the fourth analysis model 1440 may be trained.

Based on the characteristic information of the pathology image, one or more of the plurality of analysis models 1410 to 1440 included in the pathology image analysis model 1400 may be loaded.

Figure 15:
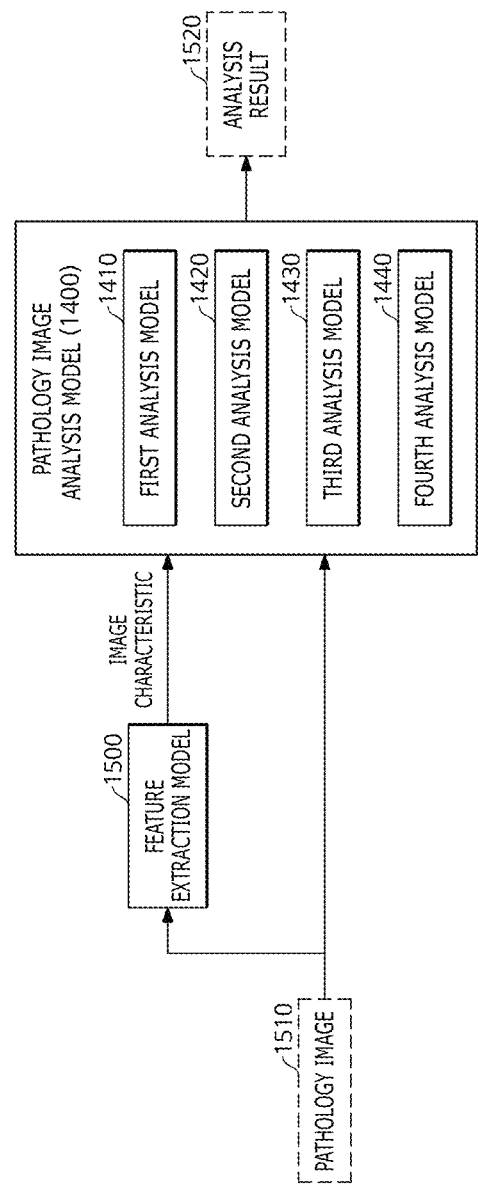
FIG. 15 illustrates a process in which an analysis result for pathology images is output through an analysis model loaded based on the characteristics of the pathology image, according to another example of the present disclosure.

FIG. 15 illustrates a process in which an analysis result 1520 for pathology images is output through an analysis model loaded based on the characteristics of pathology images 1510, according to another example of the present disclosure. As illustrated in FIG. 15, a feature extraction model 1500 may be combined with the pathology image analysis model 1400 to extract features of the pathology image 1510. In some examples, the feature extraction model 1500 may be included in the pathology image analysis model 1400.

The feature extraction model 1500 may extract, as the features, the staining color and the location of color expression included in the pathology image. The expression location of the staining color may be at least one of the cell membrane, cell nucleus, or cytoplasm. In another example, the feature extraction model 1500 may extract organs, cancer types, staining methods, etc. as the features of pathology images. For example, the feature extraction model 1500 may store at least one of a pre-stored organ pattern, cancer type pattern, or staining method pattern, and compare the pattern present in the pathology image with the organ pattern/cancer type pattern/staining method pattern so as to extract the features from the pathology image. As another example, the feature extraction model 1500 may be implemented as a machine learning model and trained to extract from the pathology image at least one of an organ associated with the pathology image, a cancer type included in the pathology image, or a staining method of the pathology image.

Referring to FIG. 15, the pathology image 1510 may be acquired, and the pathology image 1510 may be input into the feature extraction model 1500 and the pathology image analysis model 1400, respectively. The pathology image 1510 may be an unlabeled pathology image. In addition, the pathology image may be pathology images associated with a new drug or new staining method.

The feature extraction model 1500 may extract features of the pathology image and provide the extracted features of the pathology image to the pathology image analysis model 1400. The feature extraction model 1500 may extract at least one of a staining color, an organ, a cancer type, or a staining method, as a feature of the pathology image 1510.

The pathology image analysis model 1400 may load the first analysis model 1410 and input the pathology image 1510 to the first analysis model 1410 so as to perform segmentation on at least one object related to the abnormal region included in the pathology image. In addition, the pathology image analysis model 1400 may load one of a plurality of analysis models 1420 to 1440 that output different types of analysis results based on the features of the pathology image provided from the feature extraction model 1500, and acquire the analysis result 1520 for the pathology image from the loaded analysis model 1420, 1430, or 1440. In this case, the pathology image analysis model 1400 may input the pathology image segmented through the first analysis model 1410 into the loaded analysis model 1420, 1430, or 1440.

The features of the pathology image may include staining color and/or location (e.g., cell membrane/cytoplasm/cell nucleus) of expression of the staining color. In this case, the pathology image analysis model 1400 may determine and load one of the plurality of analysis models 1420 to 1440 as the target analysis model based on the features of the pathology image. For example, if a first feature in which the expression location is the cell membrane and the staining color includes brown is provided from the feature extraction model 1500, the pathology image analysis model 1400 may determine and load the second analysis model 1420 as the target analysis model, and input the segmented pathology image to the second analysis model 1420. In this case, the second analysis model 1420 may analyse the staining intensity expressed in brown from the cell membranes in the segmented region (i.e., object) in the pathology image and output the analysis result 1520.

As another example, if a second feature in which the expression location is the cell nucleus and the staining color includes blue is provided from the feature extraction model 1500, the pathology image analysis model 1400 may determine and load the third analysis model 1430 as the target analysis model, and input the segmented pathology image into the third analysis model 1430. In this case, the third analysis model 1430 may analyse the staining intensity expressed in blue from the cell nuclei in the segmented region in the pathology image and output the analysis result 1520.

As another example, if a third feature in which the expression location is the cell nucleus and the cell membrane and the staining color includes pink is provided from the feature extraction model 1500, the pathology image analysis model 1400 may determine and load the fourth analysis model 1440 as the target analysis model, and input the segmented pathology image into the fourth analysis model 1440. In this case, the fourth analysis model 1440 may analyse the distribution of each of the cell nucleus and cell membrane expressed in pink in each segmented region in the pathology image and/or morphological features and output the result. The morphological features may mean relevance to a specific disease.

Meanwhile, the features of the pathology image may be received from a user. That is, the analysis system may receive user input information including features of the pathology image. In this case, which analysis model to load may be determined based on the features of the pathology image input by the user.

Figure 16:
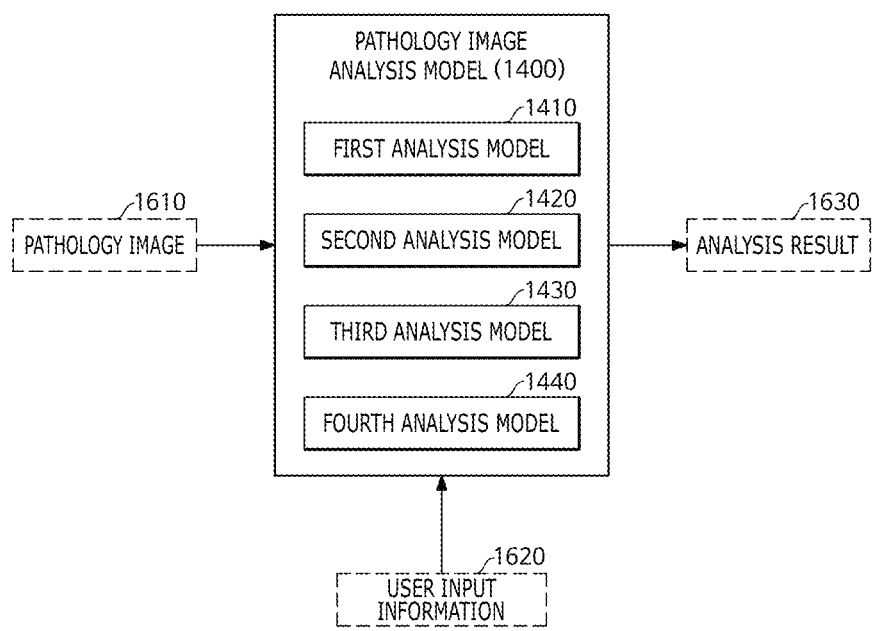
FIG. 16 illustrates a process in which an analysis result for pathology images is output through an analysis model loaded based on user input information, according to still another example of the present disclosure.

FIG. 16 illustrates a process in which the analysis result 1630 for pathology images 1610 is output through an analysis model loaded based on the user input information, according to still another example of the present disclosure. As illustrated in FIG. 16, the pathology image analysis model 1400 may acquire user input information 1620 including features of the pathology image 1610. The pathology image analysis model 1400 may load the first analysis model 1410 and input the pathology image 1610 to the first analysis model 1410 so as to perform segmentation on objects related to the abnormal region included in the pathology image.

In addition, the pathology image analysis model 1400 may determine a target analysis model to be loaded from among a plurality of analysis models based on the features of the pathology image included in the user input information 1620. The user input information 1620 may include staining color and/or location (e.g., cell membrane/cytoplasm/cell nucleus) of expression of the staining color. Additionally or alternatively, the user input information 1620 may include at least one of an organ, a cancer type, or a staining method.

The pathology image analysis model 1400 may determine and load one of the plurality of analysis models 1420 to 1440 as a target analysis model based on the features included in the user input information 1620. For example, if the user input information 1620 includes the first staining method, the pathology image analysis model 1400 may determine and load the second analysis model 1420 as the target analysis model, and input the segmented pathology image into the second analysis model 1420. In this case, the second analysis model 1420 may analyse the staining intensity expressed by the first staining method in the segmented region in the pathology image and output the analysis result 1630.

As another example, if the user input information 1620 includes the second staining method, the pathology image analysis model 1400 may determine and load the third analysis model 1430 as the target analysis model, and input the segmented pathology image into the third analysis model 1430. In this case, the second analysis model 1430 may analyse the staining intensity expressed by the second staining method in the segmented region in the pathology image and output the analysis result 1630.

As still another example, if the user input information 1620 includes the third staining method, the pathology image analysis model 1400 may determine and load the fourth analysis model 1440 as the target analysis model, and input the segmented pathology image into the fourth analysis model 1440. In this case, the fourth analysis model 1440 may output the analysis result 1630 including the distribution and/or morphological features of the color expressed by the third staining method in the segmented region in the pathology image.

As described above, if the plurality of analysis models 1410 to 1440 are included in the pathology image analysis model 1400, the pathology image analysis model 1400 may output appropriate analysis result for various cells stained according to various staining methods. Accordingly, the pathology image analysis model 1400 according to the present disclosure may be applied universally and used in various environments.

Hereinafter, various types of analysis results output through the pathology image analysis model 1400 will be described with reference to FIGS. 17 to 20.

FIGS. 17 to 20 illustrate various types of analysis results output from the pathology image analysis model 1400. FIGS. 17 to 20 illustrate at least one object (e.g., cell, tissue, or structure) identified in the pathology image with an oval.

Figure 17:
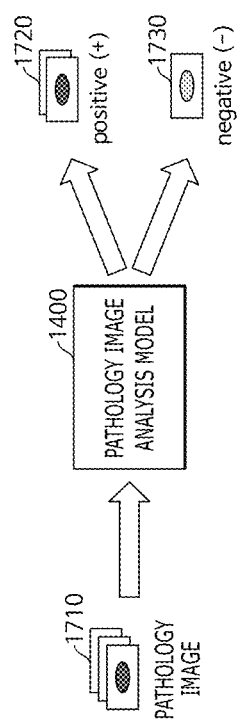
FIGS. 17 to 20 illustrate various types of analysis result output from a pathology image analysis model.

As illustrated in FIG. 17, the pathology image analysis model 1400 may receive a plurality of pathology images 1710 and determine whether staining expression of the object included in each of the pathology images 1710 is positive or negative, and output the determined results 1720 and 1730. As used herein, "positive" may mean that the protein that is the target of staining is present on the object, and "negative" may mean that the protein that is the target of staining is not present on the object. FIG. 17 illustrates that the pathology image 1720 determined as positive and the pathology image 1730 determined as negative are output separately.

Figure 18:
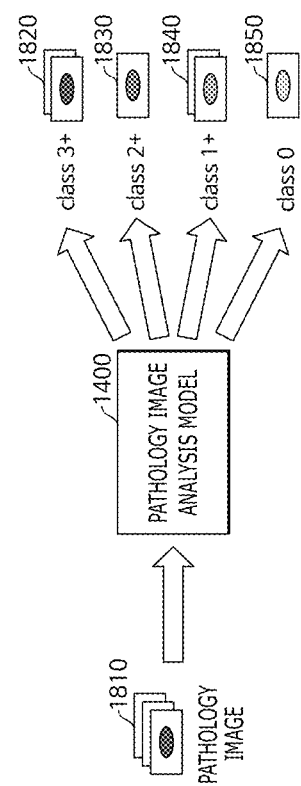

As illustrated in FIG. 18, the pathology image analysis model 1400 may receive a plurality of pathology images 1810, determine the staining expression grade for at least one object included in each of the pathology images 1810, and output an analysis result including the determined expression grades 1820 to 1850. FIG. 18 illustrates that class 3+ is the most highly expressed object, and class 0 is the least expressed object. The class 0 may mean that the protein that is the target of staining is not present on the object.

Figure 19:
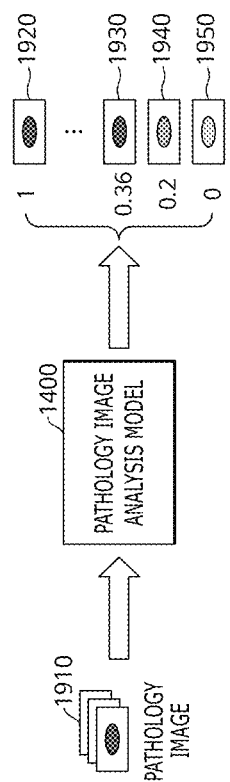

As illustrated in FIG. 19, the pathology image analysis model 1400 receives a plurality of pathology images 1910 and quantify the expression value of the object included in each of the pathology images 1910 as a number included in a predetermined range (e.g., 0 to 1), and output an analysis result including the expression values 1920 to 1950 for each object. FIG. 19 illustrates that the degree of staining expression increases as the expression value approaches 1.

Figure 20:
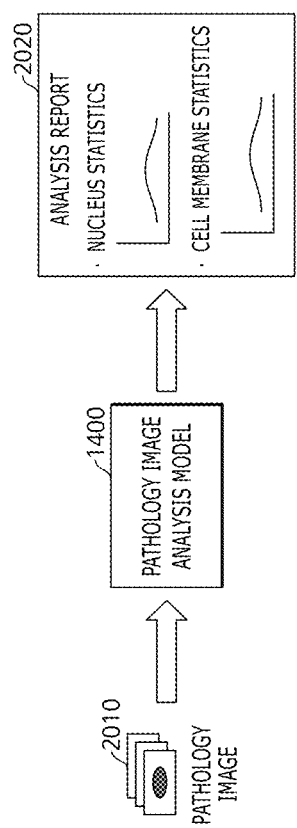

As illustrated in FIG. 20, the pathology image analysis model 1400 may receive a plurality of pathology images 2010 and output an analysis result 2020 including expression statistical information of the object included in each pathology image. FIG. 20 illustrates the analysis result 2020 including statistical information on positive or negative/grade/distribution of expression values of the cell nucleus and statistical information on positive or negative/grade/distribution of expression values of the cell membrane. In addition, the statistical information on various cells, tissues, or structures may be output through the pathology image analysis model 1400.

Figure 21:
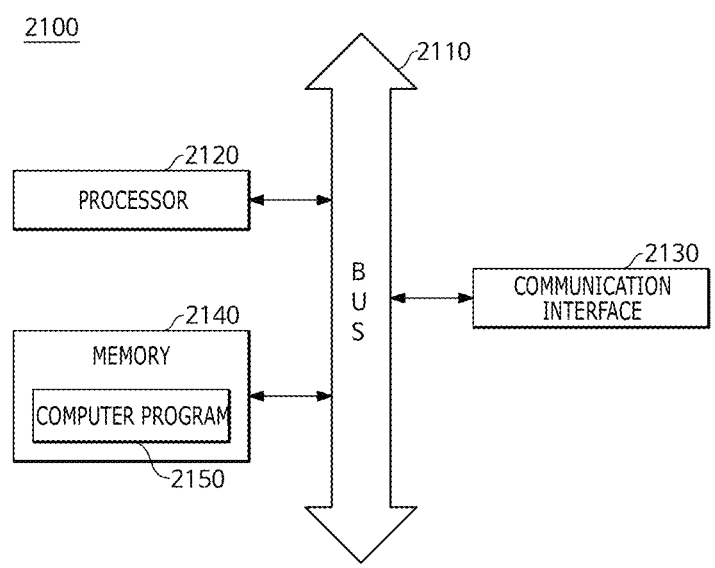
FIG. 21 is a diagram of an exemplary system configuration for analysing pathology images.

FIG. 21 is a diagram of an exemplary system configuration for analysing pathology images. An information processing system 2100 of FIG. 21 may be an example of the analysis system 510 illustrated in FIG. 5. As illustrated, the information processing system 2100 includes one or more processors 2120, a bus 2110, a communication interface 2130, and a memory 2140 for loading a computer program 2150 executed by the processor 2120. Meanwhile, only the components related to the present example are illustrated in FIG. 21. Accordingly, those of ordinary skill in the art to which the present disclosure pertains will be able to recognize that other general-purpose components may be further included in addition to the components illustrated in FIG. 21.

The processor 2120 controls the overall operation of components of the information processing system 2100. In present disclosure, the processor 2120 may be configured with a plurality of processors. The processor 2120 may include central processing unit (CPU), micro processor unit (MPU), micro controller unit (MCU), graphic processing unit (GPU), field programmable gate array (FPGA), at least two of any types of processors well known in the technical field of the present disclosure. In addition, the processor 2120 may perform computation on at least one application or program for executing the method according to various examples.

The memory 2140 may store various types of data, instructions, and/or information. The memory 2140 may load one or more computer programs 2150 in order to execute the method/operation according to various examples. The memory 2140 may be implemented as a volatile memory such as RAM, but the technical scope of the present disclosure is not limited thereto. For example, the memory 2140 may include a nonvolatile memory such as a read only memory (ROM), an erasable programmable ROM (EPROM), an electrically erasable programmable ROM (EEPROM), a flash memory, and the like, a hard disk, a detachable disk, or any type of computer-readable recording medium well known in the art to which the present disclosure pertains.

The bus 2110 may provide a communication function between components of the information processing system. The bus 2110 may be implemented as various types of buses such as an address bus, a data bus, a control bus, etc.

The communication interface 2130 may support wired/wireless Internet communication of the information processing system. In addition, the communication interface 2130 may support various other communication methods in addition to the Internet communication. To this end, the communication interface 2130 may include a communication module well known in the technical field of the present disclosure.

The computer program 2150 may include one or more instructions that cause the processors 2120 to perform operations/methods in accordance with various examples. That is, the processors 2120 may execute the one or more instructions so as to perform operations/methods according to various examples. For example, the computer program 2150 may include one or more instructions for performing operations of acquiring pathology images, inputting the acquired pathology images into a machine learning model and acquiring an analysis result for the pathology images from the machine learning model, and outputting the acquired analysis result, etc. The machine learning model may be a model trained by using a training data set generated based on a first pathology data set associated with a first domain and a second pathology data set associated with a second domain different from the first domain. In this case, a system for analysing pathology images may be implemented through the information processing system 2100 according to some examples of the present disclosure.

The above description of the present disclosure is provided to enable those skilled in the art to make or use the present disclosure. Various modifications of the present disclosure will be readily apparent to those skilled in the art, and the general principles defined herein may be applied to various modifications without departing from the spirit or scope of the present disclosure. Thus, the present disclosure is not intended to be limited to the examples described herein but is intended to be accorded the broadest scope consistent with the principles and novel features disclosed herein.

Although example implementations may refer to utilizing aspects of the presently disclosed subject matter in the context of one or more standalone computer systems, the subject matter is not so limited, and they may be implemented in conjunction with any computing environment, such as a network or distributed computing environment. Furthermore, aspects of the presently disclosed subject matter may be implemented in or across a plurality of processing chips or devices, and storage may be similarly influenced across a plurality of devices. Such devices may include PCs, network servers, and handheld devices.

While the present disclosure has been described in connection with some examples herein, it should be understood that various modifications and changes may be made without departing from the scope of the present disclosure as would be understood by those skilled in the art. Further, such modifications and changes are intended to fall within the scope of the claims appended herein.

The invention claimed is:

1. A method for analysing a pathology image, the method being performed by at least one processor and comprising:
   acquiring a pathology image;
   generating an analysis result for the pathology image based on the pathology image by using a pathology image analysis model configured to:
      generate a first analysis result by analysing a staining intensity at a first location where a staining color is expressed on at least one cell;
      generate a second analysis result by analysing a staining intensity at a second location where the staining color is expressed on the at least one cell;
      classify a first cell and a second cell in the pathology image based on staining intensity amounts at the first location on the first cell and the first location on the second cell in the pathology image;
      segment the pathology image into a first segment corresponding to the first cell and a second segment corresponding to the second cell; and
      visualize the first segment in a first color, and the second segment in a second color different from the first color; and
   outputting the analysis result including at least one of the first analysis result or the second analysis result,
   wherein the first location and the second location include at least one of cell membrane, cell nucleus, or cytoplasm.

2. The method according to claim 1, wherein the pathology image analysis model includes a plurality of analysis models, and
   the method further comprises
   determining a first analysis model for the first analysis result from the plurality of analysis models based on features of the pathology image.

3. The method according to claim 1, wherein the pathology image analysis model is further configured to receive a user input about features of the pathology image and output the analysis result based on the pathology image and the features of pathology image input by a user.

4. The method according to claim 3, wherein the features of the pathology image input by the user include at least one of the first location or the second location where the staining color is expressed.

5. The method according to claim 1, wherein the pathology image analysis model is further configured to determine whether staining expression of at least one of the first cell or the second cell is positive or negative, and output the first analysis result including whether the staining expression is positive or negative.

6. The method according to claim 1, wherein the pathology image analysis model is further configured to determine staining expression grades for the first cell and the second cell and output the first analysis result including the staining expression grades.

7. The method according to claim 1, wherein
   the pathology image analysis model is further configured to quantify a staining color expression value for each of a plurality of cells in the pathology image as a number within a predetermined range, and generate the first analysis result including each staining color expression value.

8. The method according to claim 1, wherein the pathology image analysis model is further configured to output the first analysis result including statistical information on expression of a plurality of cells in the pathology image.

9. The method according to claim 1, wherein the pathology image analysis model is further configured to output the analysis result including a distribution of staining color expression values of at least one of cell nucleus, cytoplasm, or cell membrane.

10. A computer-readable non-transitory recording medium storing instructions for causing performance of the method according to claim 1 on a computer.

11. An information processing system, comprising:
    at least one memory storing instructions; and
    at least one processor operatively connected to the at least one memory and configured to execute the instructions to:
       acquire a pathology image;
       generate an analysis result for the pathology image based on the pathology image by using a pathology image analysis model configured to:
          generate a first analysis result by analysing a staining intensity at a first location where a staining color is expressed on at least one cell;
          generate a second analysis result by analysing a staining intensity at a second location where the staining color is expressed on the at least one cell;
          classify a first cell and a second cell in the pathology image based on staining intensity amounts at the first location on the first cell and the first location on the second cell in the pathology image;

segment the pathology image into a first segment corresponding to the first cell and a second segment corresponding to the second cell; and visualize the first segment in a first color, and the second segment in a second color different from the first color; and output the analysis result including at least one of the first analysis result or the second analysis result, wherein the first location and the second location include at least one of cell membrane, cell nucleus, or cytoplasm.

12. The information processing system according to claim 11, wherein the pathology image analysis model includes plurality of analysis models and wherein the at least one processor is further configured to execute the instructions to:

determine a first analysis model for the first analysis result from the plurality of analysis models based on features of the pathology image.

13. The information processing system according to claim 11, wherein the pathology image analysis model is further configured to receive a user input about features of the pathology image and output the analysis result based on the pathology image and the features of pathology image input by a user.

14. The information processing system according to claim 13, wherein the features of the pathology image input by the user include at least one of the first location or the second location where the staining color is expressed.

15. The information processing system according to claim 11, wherein the pathology image analysis model is further configured to determine whether staining expression of at least one of the first cell or the second cell is positive or negative, and output the first analysis result including whether the staining expression is positive or negative.

16. The information processing system according to claim 11, wherein the pathology image analysis model is further configured to determine staining expression grades for the first cell and the second cell and output the first analysis result including the staining expression grades.

17. The information processing system according to claim 11, wherein the pathology image analysis model is further configured to quantify a staining color expression value for each of a plurality of cells in the pathology image as a number within a predetermined range, and generate the first analysis result including each staining color expression value.

18. The information processing system according to claim 11, wherein the pathology image analysis model is further configured to output the analysis result including a distribution of staining color expression values of at least one of cell nucleus, cytoplasm, or cell membrane.

* * * * *